US010212298B2

(12) United States Patent
 Matsumoto et al.

(10) Patent No.: US 10,212,298 B2
(45) Date of Patent: *Feb. 19, 2019

(54) SHEET DISCRIMINATOR, IMAGE FORMING APPARATUS INCORPORATING SAME, AND IMAGE FORMING SYSTEM INCORPORATING SAME TO DISTINGUISH SHEET TYPES

(71) Applicants: Tohru Matsumoto, Ibaraki (JP); Tetsuya Ofuchi, Kanagawa (JP); Takayuki Nishimura, Kanagawa (JP); Yukifumi Kobayashi, Kanagawa (JP)

(72) Inventors: Tohru Matsumoto, Ibaraki (JP); Tetsuya Ofuchi, Kanagawa (JP); Takayuki Nishimura, Kanagawa (JP); Yukifumi Kobayashi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/557,603

(22) Filed: Dec. 2, 2014

(65) Prior Publication Data
 US 2015/0151938 A1 Jun. 4, 2015

(30) Foreign Application Priority Data
 Dec. 3, 2013 (JP) ................................. 2013-250141

(51) Int. Cl.
 *H04N 1/00* (2006.01)
 *B41J 11/00* (2006.01)
 (Continued)

(52) U.S. Cl.
 CPC ........ *H04N 1/00724* (2013.01); *B41J 11/009* (2013.01); *B65H 7/14* (2013.01);
 (Continued)

(58) Field of Classification Search
 CPC .......................... H04N 1/00724; B41J 11/009
 See application file for complete search history.

(56) References Cited

U.S. PATENT DOCUMENTS

2002/0196716 A1* 12/2002 Morisaki .............. G11B 15/689
 369/30.35
2003/0066200 A1 4/2003 Hellstrom
 (Continued)

FOREIGN PATENT DOCUMENTS

JP 2005-505765 A 2/2005
JP 2005-83850 A 3/2005
 (Continued)

OTHER PUBLICATIONS

Office Action for Corresponding Japanese Patent Application No. 2013-250141 dated Aug. 4, 2017.

*Primary Examiner* — Nicholas Pachol
(74) *Attorney, Agent, or Firm* — Harness, Dickey & Pierce, P.L.C.

(57) ABSTRACT

A sheet discriminator, which is incorporated in an image forming apparatus and an image forming system, includes a sheet loader on which a recording medium is loaded, an information detector including a light emitter to emit light to a surface of the recording medium loaded on the sheet loader and a light receiver to receive the light emitted by the light emitter and detecting information of the recording medium, a sheet distinguisher to distinguish a type of the recording medium based on the information detected by the information detector, and a light emission controller to control activation and stop of the light emitter and activate the light emitter before the information detector starts detection of the information of the recording medium.

13 Claims, 15 Drawing Sheets

(51) Int. Cl.

| | |
|---|---|
| *G01N 21/55* | (2014.01) |
| *G01N 21/86* | (2006.01) |
| *G06K 15/16* | (2006.01) |
| *G01N 21/21* | (2006.01) |
| *G01N 21/47* | (2006.01) |
| *B65H 7/14* | (2006.01) |
| *H04N 1/21* | (2006.01) |

(52) U.S. Cl.
CPC ............ *G01N 21/55* (2013.01); *G01N 21/86* (2013.01); *G06K 15/16* (2013.01); *H04N 1/00588* (2013.01); *H04N 1/212* (2013.01); *H04N 1/2112* (2013.01); *B65H 2553/41* (2013.01); *G01N 21/474* (2013.01); *G01N 2021/217* (2013.01); *G01N 2021/556* (2013.01); *G01N 2021/8609* (2013.01); *G01N 2021/8663* (2013.01)

(56) References Cited

U.S. PATENT DOCUMENTS

| | | | |
|---|---|---|---|
| 2003/0103133 A1* | 6/2003 | Ueda .................. | B41J 2/325 347/219 |
| 2004/0017036 A1* | 1/2004 | Im ..................... | B65H 7/14 271/110 |
| 2005/0051743 A1 | 3/2005 | Yamaguchi | |
| 2006/0188272 A1* | 8/2006 | Triplett .............. | G03G 15/6502 399/16 |
| 2007/0019024 A1* | 1/2007 | Sanpei et al. ................ | 347/16 |
| 2008/0193157 A1* | 8/2008 | Shelton et al. ................ | 399/82 |
| 2008/0240750 A1* | 10/2008 | Hanamoto et al. ............ | 399/45 |
| 2008/0310863 A1* | 12/2008 | Honguh ................ | B65H 7/14 399/16 |
| 2009/0103148 A1* | 4/2009 | Murakami ........ | H04N 1/00352 358/498 |
| 2010/0316399 A1* | 12/2010 | Hanamoto et al. ............ | 399/45 |
| 2011/0020021 A1* | 1/2011 | Murakami ..................... | 399/45 |
| 2011/0052085 A1* | 3/2011 | Ikari et al. .................... | 382/224 |
| 2012/0002227 A1* | 1/2012 | Ogino ......................... | 358/1.12 |
| 2012/0038943 A1* | 2/2012 | Hakamada ................. | 358/1.13 |
| 2012/0134693 A1 | 5/2012 | Hoshi et al. | |
| 2013/0057861 A1 | 3/2013 | Ishii et al. | |
| 2013/0057868 A1* | 3/2013 | Oba .................. | G01N 21/4738 356/445 |
| 2013/0194573 A1 | 8/2013 | Ohba et al. | |
| 2013/0216245 A1 | 8/2013 | Hoshi et al. | |
| 2013/0216246 A1 | 8/2013 | Hoshi et al. | |
| 2013/0216247 A1 | 8/2013 | Oba et al. | |
| 2013/0228674 A1 | 9/2013 | Oba et al. | |
| 2013/0235377 A1 | 9/2013 | Ishii et al. | |
| 2014/0192361 A1* | 7/2014 | Endo et al. .................. | 356/446 |
| 2014/0241742 A1 | 8/2014 | Hoshi et al. | |
| 2014/0268151 A1 | 9/2014 | Ohba et al. | |
| 2015/0102085 A1* | 4/2015 | Balili et al. .................. | 227/39 |
| 2015/0102548 A1* | 4/2015 | Balili et al. .................. | 270/58.09 |
| 2015/0104202 A1* | 4/2015 | Caneza et al. ............... | 399/16 |

FOREIGN PATENT DOCUMENTS

| | | |
|---|---|---|
| JP | 2007-233186 | 9/2007 |
| JP | 2012-208103 | 10/2012 |

* cited by examiner

SHEET DISCRIMINATOR, IMAGE FORMING APPARATUS INCORPORATING SAME, AND IMAGE FORMING SYSTEM INCORPORATING SAME TO DISTINGUISH SHEET TYPES

CROSS-REFERENCE TO RELATED APPLICATIONS

This patent application is based on and claims priority pursuant to 35 U.S.C. § 119(a) to Japanese Patent Application No. 2013-250141, filed on Dec. 3, 2013, in the Japan Patent Office, the entire disclosure of which is hereby incorporated by reference herein.

BACKGROUND

Technical Field

This disclosure relates to a sheet discriminator to discriminate sheet types, an image forming apparatus including the sheet discriminator, and an image forming system incorporating the sheet discriminator included in the image forming apparatus.

Related Art

In known image forming processes, to achieve higher printing quality, an image forming apparatus automatically discriminates sheet types and sets image forming conditions according to the detected sheet type.

An example of an image forming apparatus shows a configuration in which a sheet discriminator is disposed inside the image forming apparatus to discriminate information of a sheet being conveyed in a sheet conveying path.

This sheet discriminator includes an optical sensor that functions as an information detector to detect information of the sheet and that has a light emitting element and a light receiving element therein. The sheet discriminator causes the light emitting element of the optical sensor to emit light and the light receiving element of the optical sensor to receive the light reflected on a surface of the sheet traveling in the sheet conveying path, and detects sheet information based on optical information including a light amount of the received light.

Accordingly, based on the sheet information thus detected by the optical sensor, a controller that functions as a sheet distinguisher to distinguish the sheet types, the image forming apparatus sets the image forming conditions according to the sheet type.

SUMMARY

At least one aspect of this disclosure provides a sheet discriminator including a sheet loader on which a recording medium is loaded, an information detector including a light emitter to emit light to a surface of the recording medium loaded on the sheet loader and a light receiver to receive the light emitted by the light emitter and detecting information of the recording medium, a sheet distinguisher to distinguish a type of the recording medium based on the information detected by the information detector, and a light emission controller to control activation and stop of the light emitter and activate the light emitter before the information detector starts detection of the information of the recording medium.

DETAILED DESCRIPTION

Figure 1:
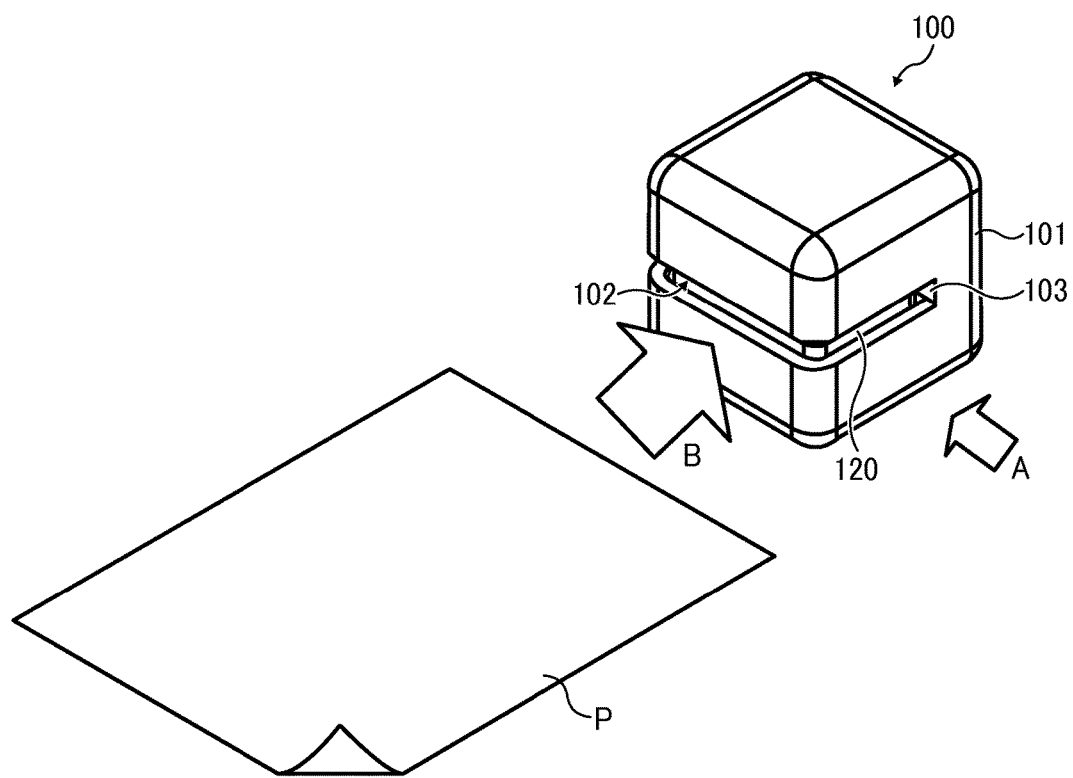
FIG. 1 is a diagram illustrating a configuration of a sheet discriminator according to an example of this disclosure.

It will be understood that if an element or layer is referred to as being "on", "against", "connected to" or "coupled to" another element or layer, then it can be directly on, against, connected or coupled to the other element or layer, or intervening elements or layers may be present. In contrast, if an element is referred to as being "directly on", "directly connected to" or "directly coupled to" another element or layer, then there are no intervening elements or layers present. Like numbers referred to like elements throughout.

As used herein, the term "and/or" includes any and all combinations of one or more of the associated listed items.

Spatially relative terms, such as "beneath", "below", "lower", "above", "upper" and the like may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements describes as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors herein interpreted accordingly.

Although the terms first, second, etc. may be used herein to describe various elements, components, regions, layers and/or sections, it should be understood that these elements, components, regions, layer and/or sections should not be limited by these terms. These terms are used to distinguish one element, component, region, layer or section from another region, layer or section. Thus, a first element, component, region, layer or section discussed below could be termed a second element, component, region, layer or section without departing from the teachings of the present disclosure.

The terminology used herein is for describing particular embodiments and examples and is not intended to be limiting of exemplary embodiments of this disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Descriptions are given, with reference to the accompanying drawings, of examples, exemplary embodiments, modification of exemplary embodiments, etc., of an image forming apparatus according to exemplary embodiments of this disclosure. Elements having the same functions and shapes are denoted by the same reference numerals throughout the specification and redundant descriptions are omitted. Elements that do not demand descriptions may be omitted from the drawings as a matter of convenience. Reference numerals of elements extracted from the patent publications are in parentheses so as to be distinguished from those of exemplary embodiments of this disclosure.

This disclosure is applicable to any image forming apparatus, and is implemented in the most effective manner in an electrophotographic image forming apparatus.

In describing preferred embodiments illustrated in the drawings, specific terminology is employed for the sake of clarity. However, the disclosure of this disclosure is not intended to be limited to the specific terminology so selected and it is to be understood that each specific element includes any and all technical equivalents that have the same function, operate in a similar manner, and achieve a similar result.

Referring now to the drawings, wherein like reference numerals designate identical or corresponding parts throughout the several views, preferred embodiments of this disclosure are described.

It is to be noted in the following examples that the term "sheet" is not limited to indicate a paper material but also includes OHP (overhead projector) transparencies, OHP film sheets, coated sheet, thick paper such as post card, thread, fiber, fabric, leather, metal, plastic, glass, wood, and/or ceramic by attracting developer or ink thereto, and is used as a general term of a recorded medium, recording medium, sheet member, and recording material to which the developer or ink is attracted.

First, a description is given of a comparative sheet discriminator.

When a light emitting element of an optical sensor emits light to a deformed portion of a sheet having deformation such as curl and waveform induced when the sheet is being conveyed, optical information received by the light receiving element varies according to the state of deformation. Therefore, it is likely that correct sheet information is not detected and accuracy in sheet discrimination is degraded.

The sheet discriminator is disposed not only inside an image forming apparatus but also outside the image forming apparatus.

The sheet discriminator has an external case having sidewalls. On one sidewall of the external case, an opening is provided through which the sheet is pulled out. Further, the sheet discriminator includes a sheet loading part and an optical sensor. The sheet loading part on which the sheet inserted through the opening is loaded is disposed inside the external case. The optical sensor to detect information of the sheet is disposed facing the sheet loading part.

To discriminate the sheet types, while checking that no deformation such as curl is formed on the sheet, an operator inserts the sheet into the external case via the opening. The operator then load the sheet on the sheet loading part, so that the optical sensor detects sheet information.

These actions can prevent the optical sensor from detecting information about deformed portion of the sheet. Accordingly, accurate sheet information can be detected and degradation of sheet discrimination accuracy can be restricted.

However, if the optical sensor constantly emits light so that the sheet types can be discriminated during a period of from the power on of the image forming apparatus and to the start of image forming operations, the life of the optical sensor becomes short.

Now, a description is given of a sheet discriminator 100 according to this disclosure with reference to FIGS. 1 through 18.

FIG. 1 is a diagram illustrating a configuration of the sheet discriminator 100.

The sheet discriminator 100 includes an external case 101. The external case 101 includes a sheet information detecting sensor 110, a sheet detecting sensor 140, and a sheet loading table 120 therein. The sheet information detecting sensor 110 functions as an information detector to detect information to be used to discriminate the sheet P. The sheet detecting sensor 140 detects whether there is the sheet P at a detection position. The sheet loading table 120 functions as a sheet loader on which the sheet P is located.

Figure 3:
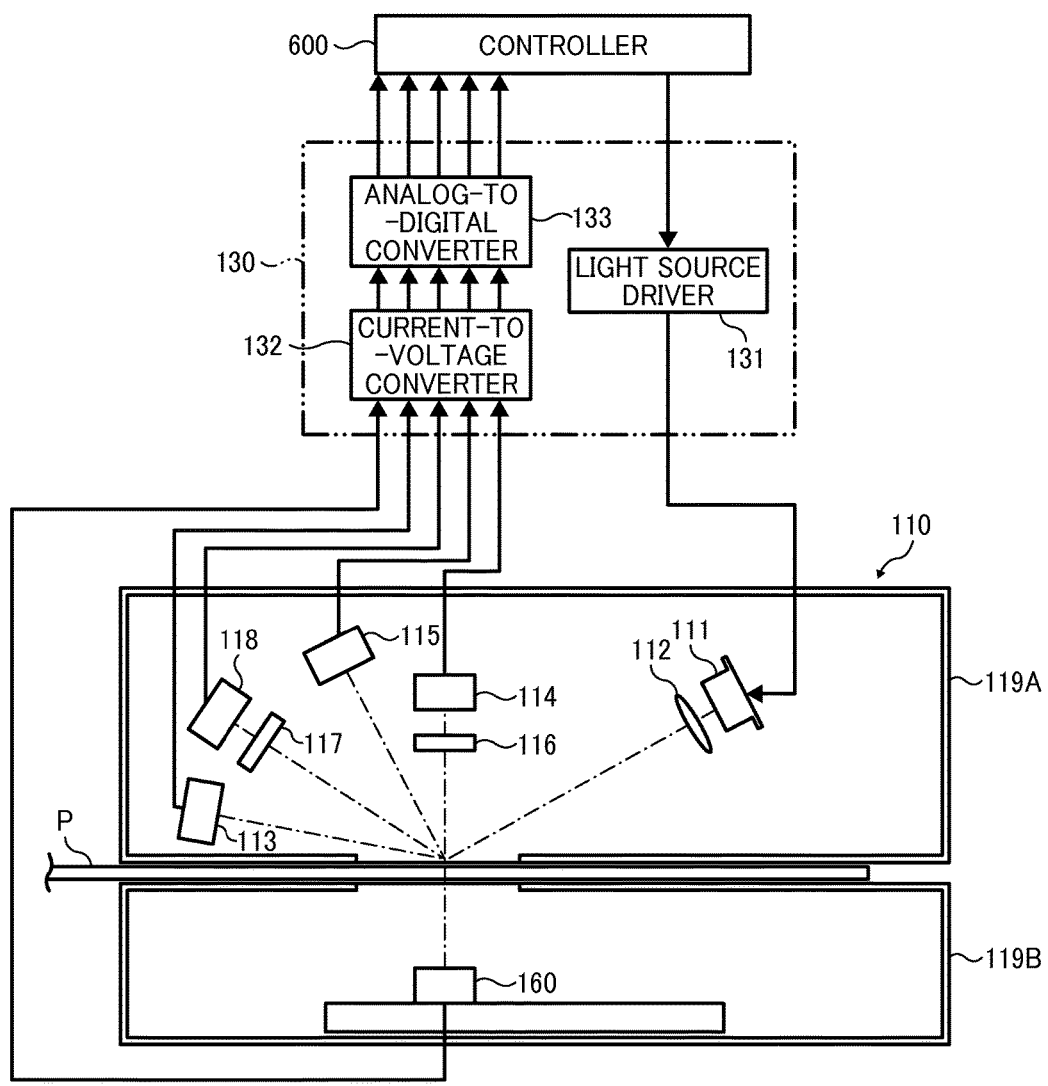
FIG. 3 is a diagram illustrating a configuration of an optical sensor and a processing device.

It is to be noted that the sheet information detecting sensor 110 and the sheet detecting sensor 140 are connected via a controller 600 that functions as a sheet distinguisher (see FIG. 3). Based on detection results obtained by the sheet detecting sensor 140, the controller 600 controls start and stop of light emission of a light source 111 (see FIG. 3) of the sheet information detecting sensor 110 via a light emission processing unit 130 that functions as a light emission controller.

The external case 101 has sidewalls. An opening 102 is formed on one of the sidewalls of the external case 101. The sheet P is inserted into and removed from the opening 102 so that the sheet P is loaded on the sheet loading table 120.

The sheet P is inserted into the opening 102 of the sheet discriminator 100 in a direction indicated by arrow B in FIG. 1 and pushed further until the sheet P contacts an end face 103 of the opening 102 or approaches the end face 103.

At this time, it is preferable that the operator grabs both left and right ends of the sheet P with respect to the direction B and inserts the sheet while checking that the sheet P has no deformation such as wrinkle or crease on the sheet P. It is to be noted that sheet insertion to the opening 102 is not limited to the above-described way but is applicable with any way of sheet insertion even if the sheet P can be inserted into the opening 102 of the sheet discriminator 100 horizontally.

To discriminate a type of the sheet P, the operator inserts the sheet P into the external case 101 via the opening while checking that there is no deformation such as curls on the sheet P. Then, the operator loads the sheet P on the sheet loading table 120, so that the sheet information detecting sensor 110 detects information of the sheet P while the sheet P is loaded on the sheet loading table 120. By so doing, the sheet information detecting sensor 110 does not detect deformed portions on the sheet P and detects correct sheet information, and therefore performance of accurate discrimination of sheet types is prevented from being degraded.

Figure 2A:
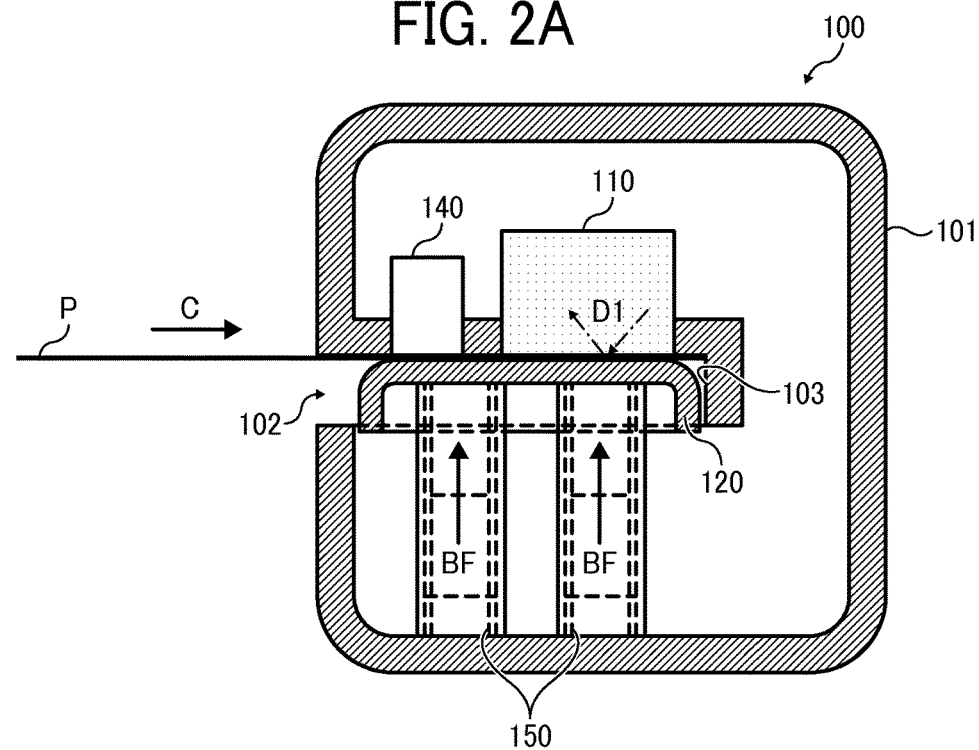
FIG. 2A is a cross sectional view illustrating the sheet discriminator when a sheet is inserted thereto through an opening.
Figure 2B:
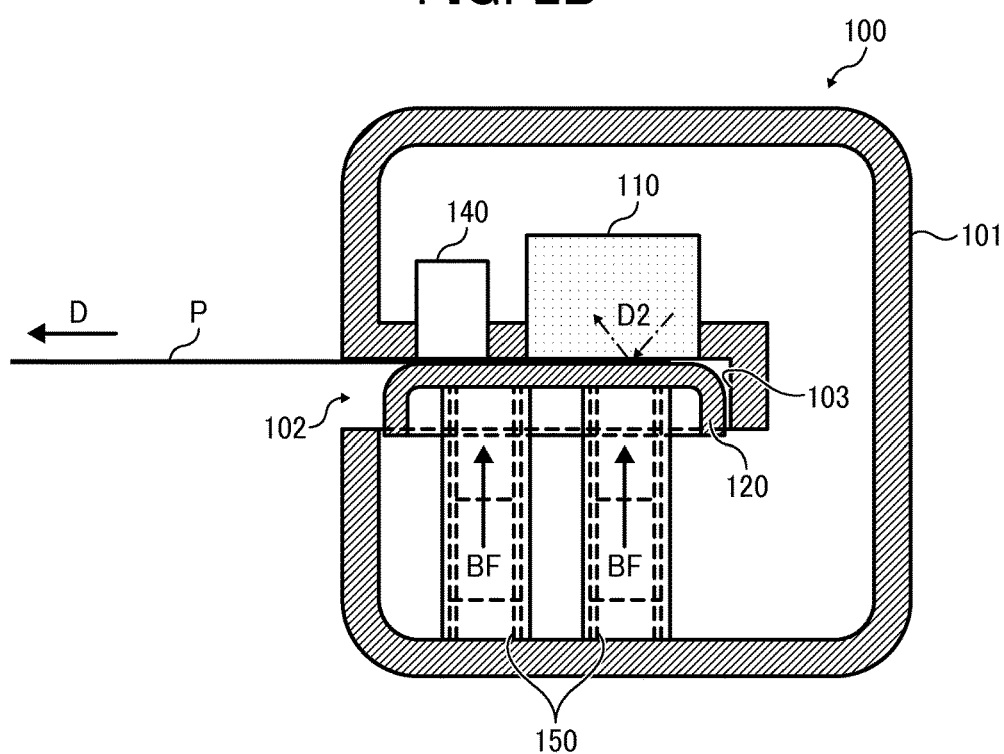
FIG. 2B is a cross sectional view illustrating the sheet discriminator when the sheet is pulled out from the opening of the sheet discriminator.

FIGS. 2A and 2B are cross sectional views of the sheet discriminator 100, viewed from a direction indicated by arrow A in FIG. 1. Specifically, FIG. 2A is a cross sectional view illustrating the sheet discriminator 100 when the sheet P is inserted thereto through the opening 102 of the sheet discriminator 100 and FIG. 2B is a cross sectional view illustrating the sheet discriminator 100 when the sheet P is pulled out from the opening 102 of the sheet discriminator 100.

The sheet detecting sensor 140 and the sheet information detecting sensor 110 are disposed in an upper part inside the external case 101 of the sheet discriminator 100 and aligned in this order in a sheet inserting direction indicated by arrow C illustrated in FIGS. 2A and 2B. The sheet loading table 120 is disposed facing the sheet information detecting sensor 110 and the sheet detecting sensor 140 across a gap in a lower part inside the external case 101 of the sheet discriminator 100.

Biasing members 150 such as spring are disposed facing the sheet information detecting sensor 110 with the sheet loading table 120 interposed therebetween. The sheet loading table 120 is biased by the biasing members 150 in a direction indicated by arrows BF in FIGS. 2A and 2B, that is, toward the sheet information detecting sensor 110.

As illustrated in FIG. 3, the sheet information detecting sensor 110 includes a light source 111, a collimator lens 112, receivers 113, 114, 115, and 118, polarizing filters 116 and 117, and dark boxes (camera obscuras) 119A and 119B to accommodate these optical units therein.

Each of the dark boxes 119A and 119B is a metal box such as an aluminum box, and anodic oxide coating with black dye on a surface thereof in order to reduce the impact of ambient light and stray light.

The light source 111 functions as a light emitter and includes multiple light emitting elements 111a, which are vertical cavity surface emitting laser (VCSEL). Specifically, the light source 111 includes a VCSEL array 111LA.

Figure 4:
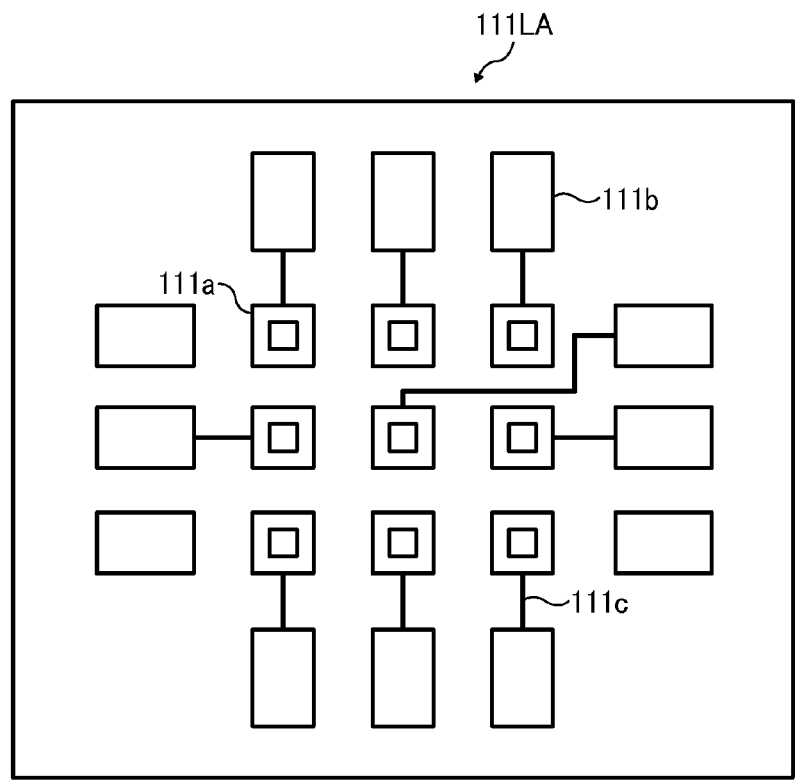
FIG. 4 is a diagram illustrating a structure of a vertical cavity surface emitting laser array (a VCSEL array)

As illustrated in FIG. 4, the light source 111 of the sheet information detecting sensor 110 includes a 2 dimensional array with nine (9) light emitting elements 111a. The VCSEL array 111LA includes electrode pads 111b and wiring members 111c. Each wiring member 111c connects one of the multiple light emitting elements 111a with a corresponding one of the electrode pads 111b.

Figure 5:
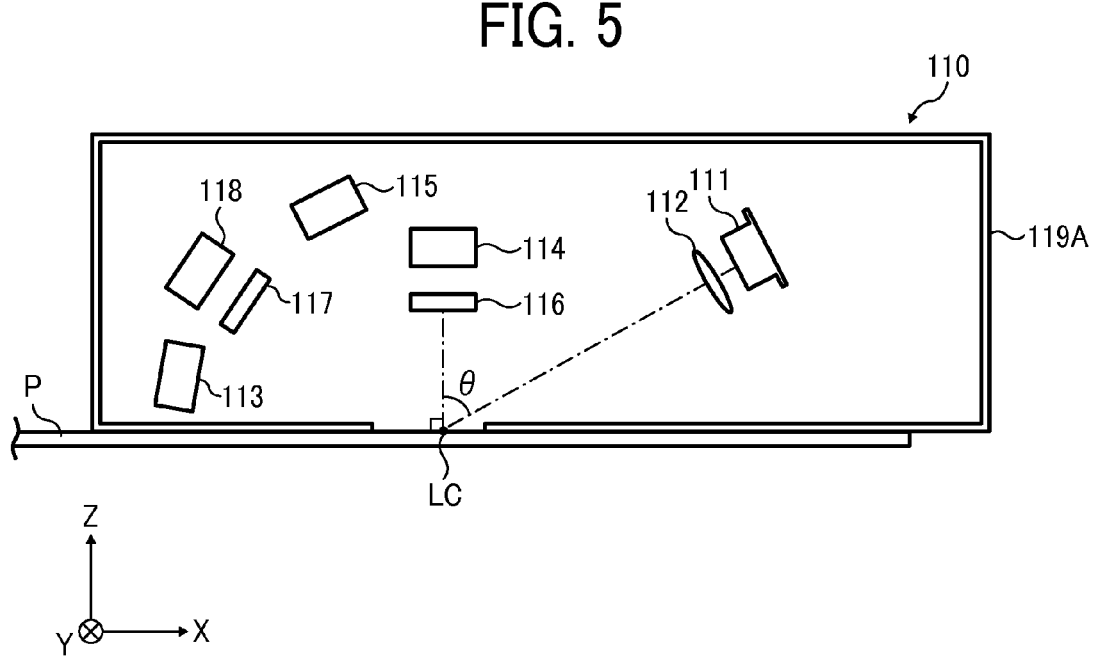
FIG. 5 is a diagram illustrating an incident angle of an irradiation light to the sheet.

The light source 111 is disposed such that linearly polarized light of S-polarized light to the sheet P is emitted. As illustrated in FIG. 5, an incidence angle θ of light from the light source 111 to the sheet P is 80 degrees. The light emission processing unit 130 turns on/off the light source 111.

The collimator lens 112 is disposed on a light path of light emitted from the light source 111 to make the light substantially parallel, which is hereinafter referred to as a substantially parallel light. The substantially parallel light has passes through the collimator lens 112 then through an opening provided on the dark box 119A, and emits the light to the sheet P. It is to be noted that a center of a light emission region on a surface of the sheet P is hereinafter referred to as a "center of light emission" and the light passed through the collimator lens 112 is also referred to as an "irradiation light".

When the light enters onto a border surface of a medium, a surface that contains an incident light (an incoming radiation) and a normal line of a border surface standing at a light incident point. When the incident light includes multiple light beams, each light beam has the plane of incidence. Here, for convenience, the plane of incidence of light incoming to the center of light emission is referred to as a plane of incidence of the sheet P. Specifically, the plane of incidence of a sheet contains the center of light emission and is parallel to X and Z surfaces of the sheet P.

It is to be noted that terms "S-polarized light" and "P-polarized light" are used for not only the incident light to the sheet P but also a reflection light on the sheet P based on a polarization direction of the incident light to the sheet P for easy understanding of this technique. On the plane of incidence, a polarization direction identical to the incident light is referred to as "S-polarized light" and a polarization direction perpendicular to the incident light is referred to as "P-polarized light".

The polarizing filter 116 is disposed on a +Z side of the center of light emission. The polarizing filter 116 is a polarizing filter that transmits the P-polarized light and blocks or reflects the S-polarized light. It is to be noted that a polarizing beam splitter that has the same functions as the polarizing filter 116 can be employed instead of the polarizing filter 116.

Figure 6:
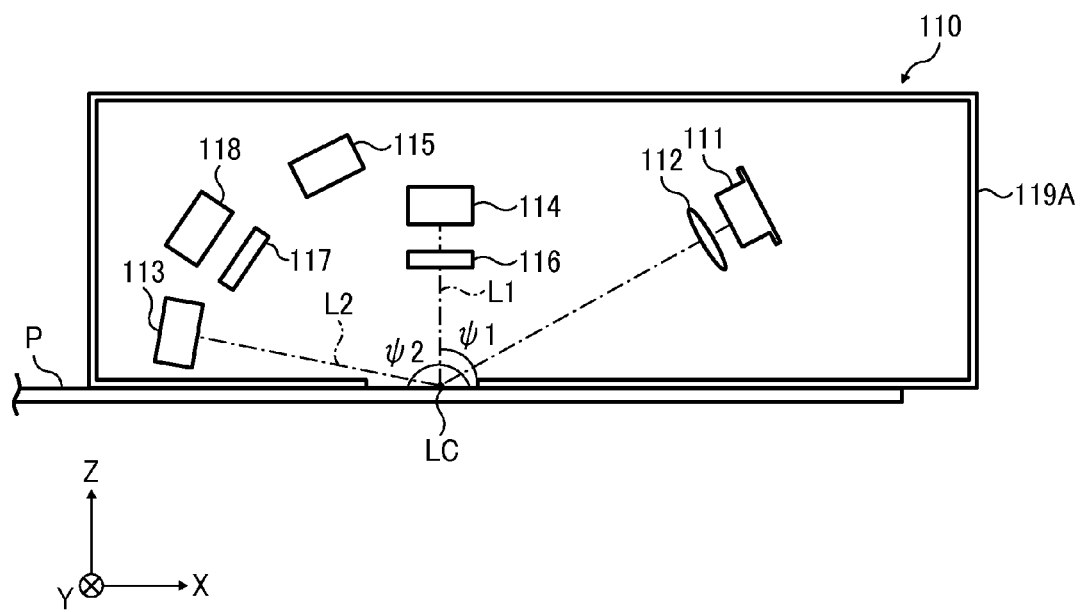
FIG. 6 is a diagram illustrating respective positions of receivers.

The receiver 114 is disposed on the +Z side of the polarizing filter 116 and functions as a light receiver to receive the light transmitted through the polarizing filter 116. As illustrated in FIG. 6, a line L1 connects the center of light emission, a center of the polarizing filter 116, and a center of the receiver 114. The line L1 and the surface of the sheet P form an angle ψ1 of 90 degrees.

The receiver 113 is disposed on the +X side of the center of light emission with respect to an X axis. As illustrated in FIG. 6, a line L2 connects the center of light emission and a center of the receiver 113. The line L2 and the surface of the sheet P form an angle ψ2 of 170 degrees.

A center of the light source 111, the center of light emission, the center of the polarizing filter 116, and respective centers of the receivers 113, 114, 115, and 118 fall on the substantially identical vertical plane.

The reflection light reflected on the sheet P when the sheet P is irradiated can be separated to reflection light reflected on the surface of the sheet P and reflection light reflected from an inside of the sheet P. Further, the reflection light reflected on the surface of the sheet P can be separated to specular reflection light (SRL) and diffused reflection light (DRL).

Figure 7A:
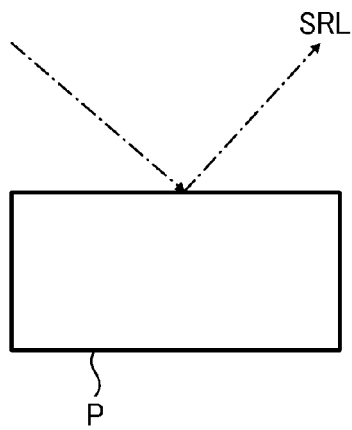
FIG. 7A is a diagram illustrating a surface specular reflection light.
Figure 7B:
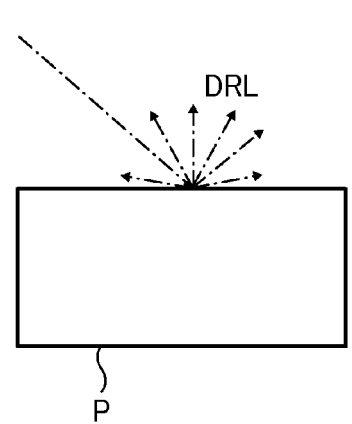
FIG. 7B is a diagram illustrating a surface diffused reflection light.
Figure 7C:
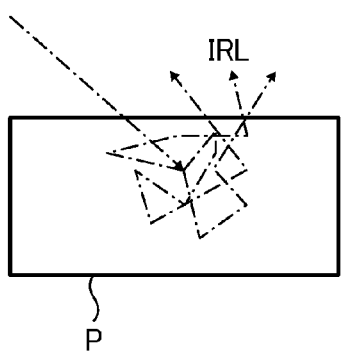
FIG. 7C is a diagram illustrating an internal reflection light.

For convenience, the specular reflection light reflected on the surface of the sheet P is hereinafter referred to as a "surface specular reflection light" (see FIG. 7A) and the diffused reflection light reflected on the surface of the sheet P is hereinafter referred to as a "surface diffused reflection light" (see FIG. 7B).

The surface of the sheet P includes plane portions and sloped portions. Based on a rate of the plane portions and the sloped portions, smoothness of the surface of the sheet P is determined. The light reflected on the plane portions becomes the surface specular reflection light and the light reflected on the sloped portions becomes the surface diffused reflection light. The surface diffused reflection light is the light fully reflected from an object (i.e., the sheet P) and a reflection direction has isotropy. As smoothness increases, the level of the surface specular reflection light rises.

By contrast, when the sheet P is a regular printing sheet, the reflection light reflected from the inside of the sheet P scatters in the fibers of the sheet P. Therefore, the reflection light is the diffused reflection light because the light scatters multiply in the sheet P. Hereinafter, for convenience, the reflection light reflected from the inside of the sheet P is also referred to as an "internal reflection light" (see FIG. 7C). Similar to the surface diffused reflection light, the internal reflection light is the light fully reflected from an object (i.e., the sheet P) and the reflection direction is isotropic.

The polarization direction of the surface specular reflection light and the surface diffused reflection light toward the receiver (i.e., the receiver 114) is the same as the polarization direction of the incident light.

In order to rotate the polarization direction on the surface of the sheet S, the incident light is reflected on the sloped surface that is slanted to the rotation of the polarization direction with respect to an incident direction. Here, since the center of the light source (i.e., the light source 111), the center of light emission, and the center of each receiver (i.e., the receivers 113 and 114) fall on the same plane, the reflection light in the polarization direction rotated on the surface of the sheet P is not reflected in any direction of the receiver.

By contrast, the polarization direction of the internal reflection light is rotated with respect to the polarization direction of the incident light. It is thought that the light entered into the inside of the sheet (i.e., the sheet P) passes through the fibers of the sheet and optically rotates during multiple scattering in the sheet, thereby rotates the polarization direction.

Figure 8:
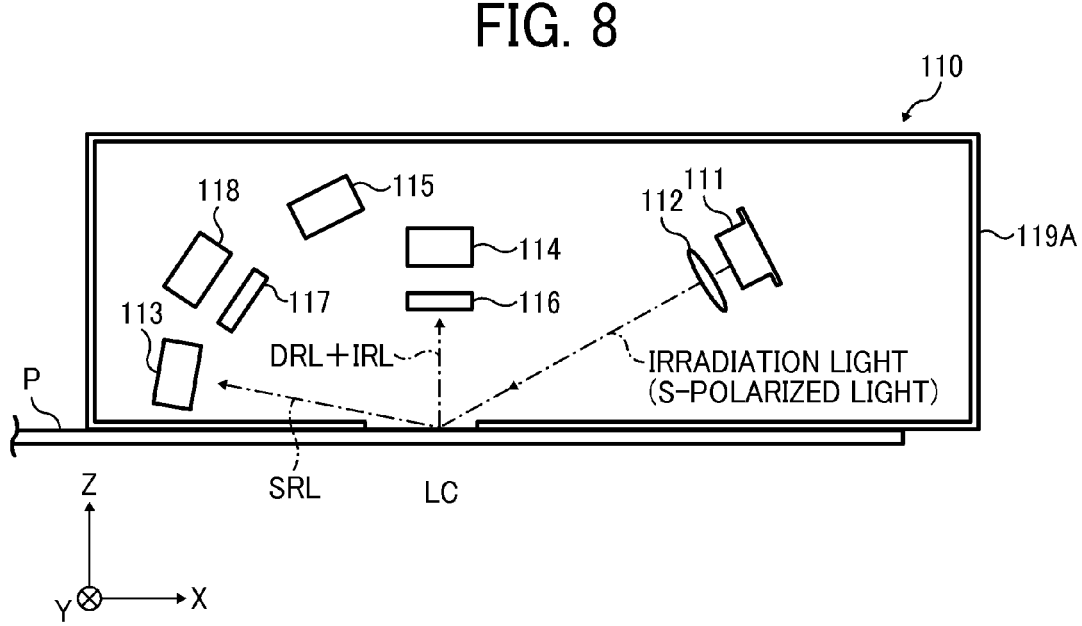
FIG. 8 is a diagram illustrating the light received by receivers.
Figure 9:
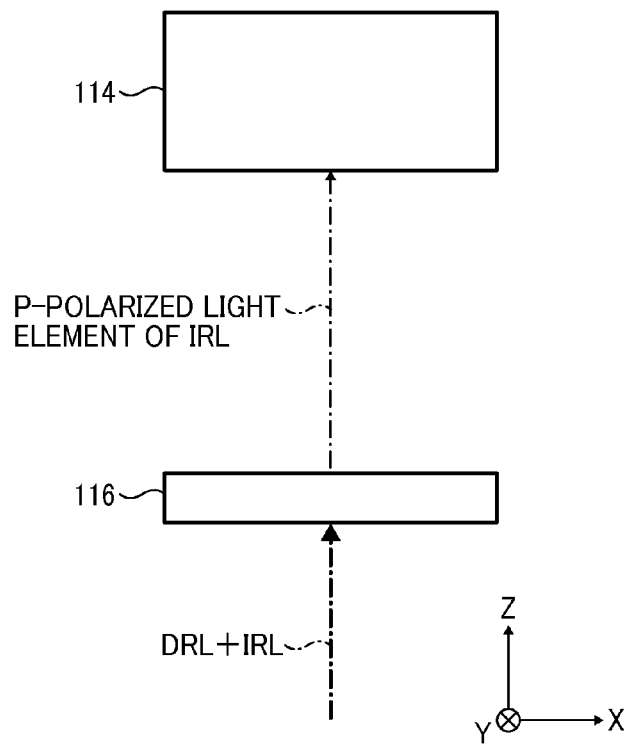
FIG. 9 is a diagram illustrating an incident light to a diffusion filter.

The reflection light including the surface diffused reflection light and the internal reflection light enters into the polarizing filter 116, as illustrated in FIG. 8.

Since the surface diffused reflection light is the S-polarized light that is the same as the incident light. Therefore, the polarizing filter 116 blocks or reflects the surface diffused reflection light. By contrast, the internal reflection light includes both the S-polarized light and the P-polarized light. Therefore, a component of the P-polarized light passes through the polarizing filter 116. Specifically, the component of the P-polarized light contained in the internal reflection light is received by the receiver 114 (see FIG. 9).

It is to be noted that the component of the P-polarized light included in the internal reflection light is also referred to as a "P-polarized light internal reflection light", for convenience. In addition, a component of the S-polarized light included in the internal reflection light is also referred to as an "S-polarized light internal reflection light".

The level of the P-polarized light internal reflection light is proved to have a correlation to thickness and density of the sheet. It is because the level of the P-polarized light internal reflection light depends on a path length when the sheet passes through the fibers in the sheet.

The receiver 113 receives reflection light having the surface specular reflection light, the surface diffused reflection light, and the internal reflection light. At this light receiving position, the level of the surface diffused reflection light and the level of the internal reflection light are significantly smaller than the level of the surface specular reflection light. Therefore, it is regarded as that the received light level substantially corresponds to the level of the surface specular reflection light (see FIG. 8).

Figure 10:
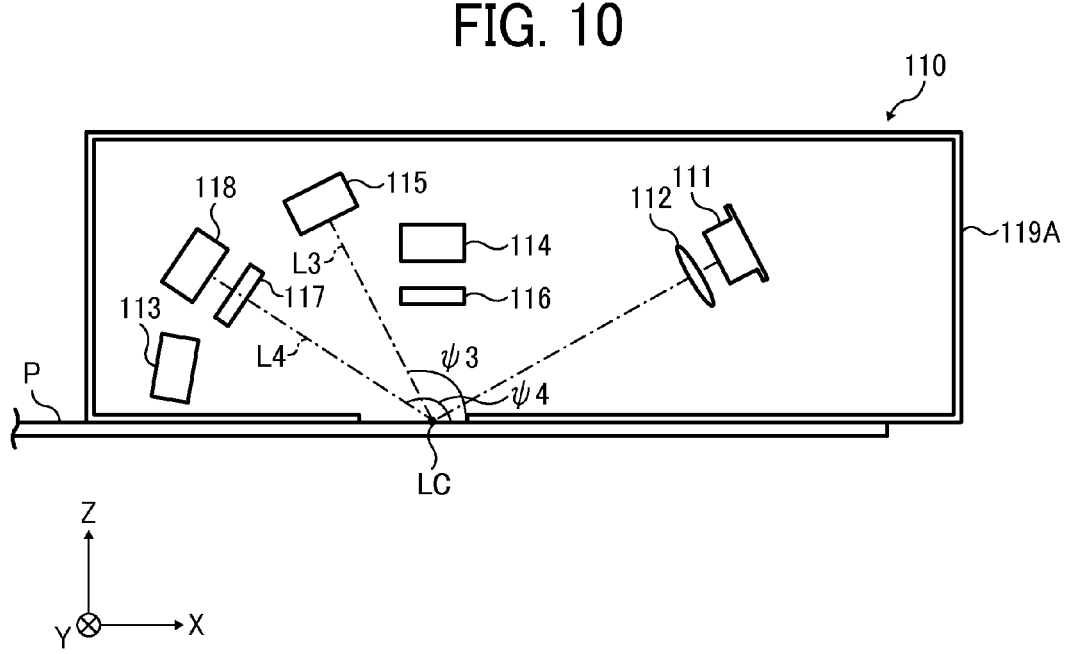
FIG. 10 is a diagram illustrating respective positions of different receivers.

The receiver 115 that functions as a light receiver is disposed at a position to receive the surface diffused reflection light and the internal reflection light. For example, as illustrated in FIG. 10, a line L3 connects the center of light emission and a center of the receiver 115. The line L3 and the surface of the sheet P form an angle ψ3 of 120 degrees. The center of the light source 111, the center of light emission, the center of the polarizing filter 116, and the respective centers of the receivers 113, 114, 115, and 118 fall on the substantially same vertical plane.

The polarizing filter 117 is disposed on the light path of the surface diffused reflection light and the internal reflection light. The polarizing filter 117 is a polarizing filter that transmits the P-polarized light and blocks or reflects the S-polarized light.

The receiver 118 is disposed on a light path of the light transmitted through the polarizing filter 117. The receiver 118 receives a component of the P-polarized light included in the internal reflection light.

For example, as illustrated in FIG. 10, a line L4 connects the center of light emission, a center of the polarizing filter 117, and a center of the receiver 118. The line L4 and the surface of the sheet P form an angle ψ4 of 150 degrees. The center of the light source 111, the center of light emission, the center of the polarizing filter 116, the center of the polarizing filter 117, and the respective centers of the receivers 113, 114, 115, and 118 fall on the substantially same vertical plane.

The receiver 160 illustrated in FIG. 3 is disposed at a position to receive a light beam that is transmitted through the sheet P out of the light beams emitted from the light source 111 and irradiated to the sheet P.

The receivers 113, 114, 115, and 118 output respective electrical signals (current signals) corresponding to respective received light levels to the light emission processing unit 130.

As illustrated in FIG. 3, the light emission processing unit 130 includes a light source driver 131, a current-to-voltage converter 132, and an analog-to-digital (AD) converter 133. The light emission processing unit 130 is connected to the dark box 119A.

The light source driver 131 outputs the light source driving signal to the light source 111 according to instructions of the controller 600.

The current-to-voltage converter 132 convers current signals inputted by each receiver to voltage signals.

The AD converter 133 converts analog signals passing through the current-to-voltage converter 132 to digital signals and outputs the converted digital signals to the controller 600.

As described in this example, by including information obtained by the receiver 160 that receives a transmitted light in addition to information obtained by the receivers 113, 114, 115, and 118 receiving the reflection light, more precise discrimination of the type of the sheet P can be achieved.

Figure 11:
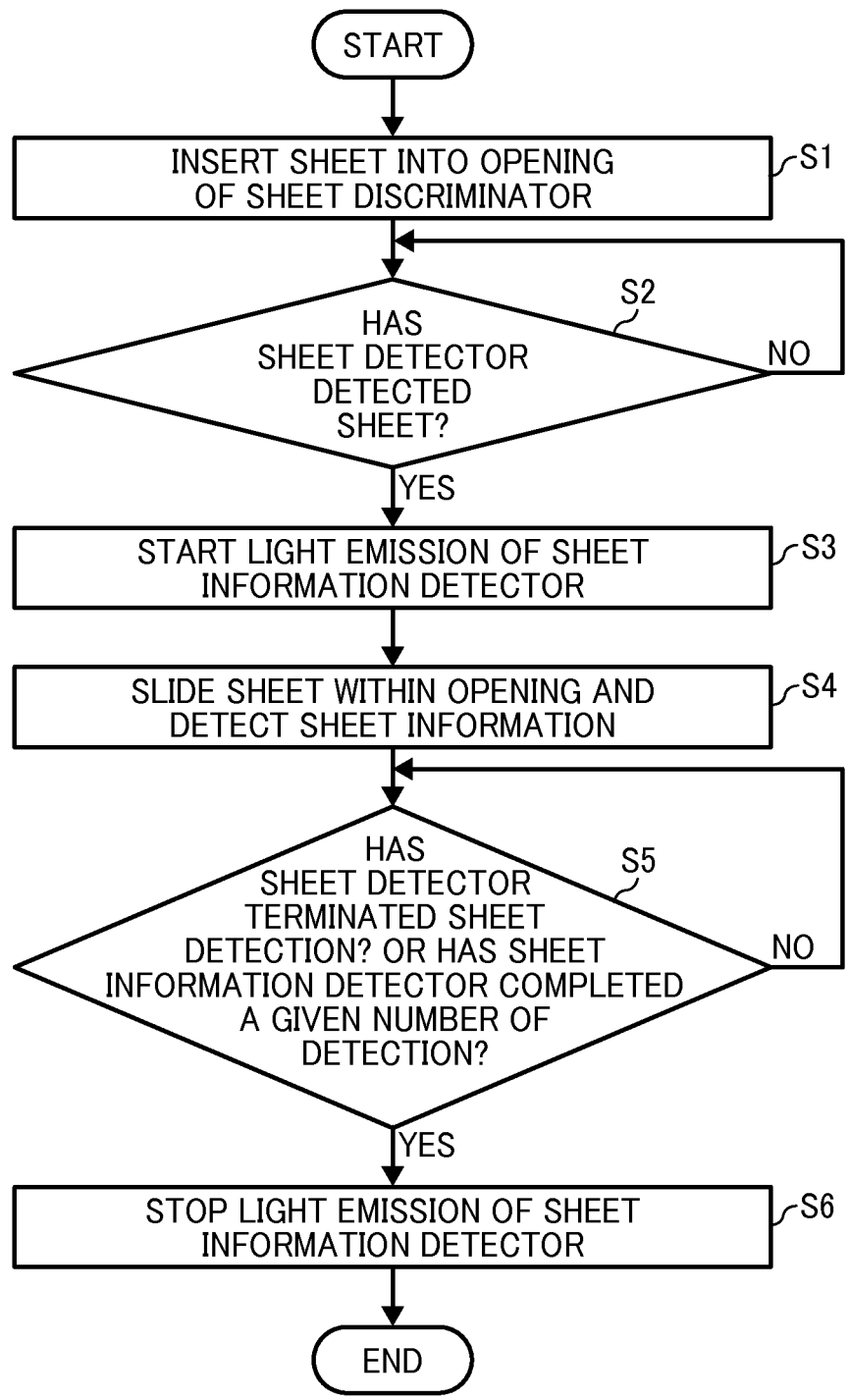
FIG. 11 is a flowchart illustrating an example of control of sheet discrimination performed by the sheet discriminator.

A description is given of a control of sheet discrimination with reference to FIGS. 2A, 2B, and 11.

FIG. 11 is a flowchart illustrating an example of control of sheet discrimination performed by the sheet discriminator 100.

As illustrated in FIG. 2A, the sheet P is inserted toward the end face 103 of the opening 102 of the sheet discriminator 100 in the direction C, as described in step S1 in FIG. 11. When the sheet detecting sensor 140 detects the sheet P, which is YES in step S2 in FIG. 11, the sheet information detecting sensor 110 starts light emission, as described in step S3 in FIG. 11. When the sheet detecting sensor 140 does not detect the sheet P, which is NO in step S2 in FIG. 11, the procedure is repeated until the sheet detecting sensor 140 detects the sheet P.

The sheet information detecting sensor 110 performs a first information detection D1 in FIG. 2A with respect to the sheet P that is further inserted toward the end face 103. After the sheet P has reached the end face 103 of the opening 102, the sheet P is removed. When pulling out the sheet P from the opening 102, the sheet P moves in a direction indicated by arrow D in FIG. 2B. At this time, the sheet information detecting sensor 110 performs a second information detection D2 in FIG. 2B. Accordingly, the sheet information detecting sensor 110 detects the sheet P at different points on the sheet P in the first information detection and the second information detection.

As described above, the sheet discriminator 100 according to this example slides the sheet P in the opening 102 for multiple detections. Based on the information obtained by the sheet information detecting sensor 110, the controller 600 discriminates the sheet P, as described in step S4 in FIG. 11.

After the sheet P is removed from the opening 102 and is not detected by the sheet detecting sensor 140, which is YES in step S5 in FIG. 11, the controller 600 causes the sheet information detecting sensor 110 to stop light emission, as described in step S6 in FIG. 11. Alternatively, after the sheet information detecting sensor 110 completes the second information detection, which is YES in step S5 in FIG. 11, the controller 600 causes the sheet information detecting sensor 110 to stop light emission, as described in step S6 in FIG. 11. When the sheet P is detected by the sheet detecting sensor 140 and the sheet information detecting sensor 110 does not complete the second information detection, which is NO in step S5 in FIG. 11, the procedure is repeated until the condition of step S5 is satisfied.

As described above, the controller 600 discriminates the sheet P based on the sheet information obtained from the multiple points on the sheet P. This operation encourages averaging discrimination results and obtaining the median value of the discrimination results, and therefore measurement errors such as noise can be reduced or prevented and more precise discrimination of the sheet P can be achieved.

Further, the sheet discriminator 100 according to this example causes the sheet information detecting sensor 110 to emit light when the sheet information detecting sensor 110 detects information of the sheet P. When compared with a case in which the sheet information detecting sensor 110 constantly emits light, the sheet discriminator 100 according to this example can extend the life of the sheet information detecting sensor 110 and reduce waste energy consumption thereof.

Further, when the sheet detecting sensor 140 detects the sheet P, the controller 600 causes the sheet information detecting sensor 110 to emit light. By so doing, when the sheet P is inserted into the opening 102 of the sheet discriminator 100, the sheet information detecting sensor 110 can start light emission without any operator handling.

Further, when the sheet detecting sensor 140 detects no sheet P, the controller 600 causes the sheet information detecting sensor 110 to stop emitting light. By so doing, when the sheet P is pulled out from the opening 102 of the sheet discriminator 100, the sheet information detecting sensor 110 can stop light emission without any operator handling.

Further, as illustrated in FIGS. 2A and 2B, the biasing member 150 presses the sheet loading table 120 toward the sheet information detecting sensor 110. By so doing, a detection face of the sheet information detecting sensor 110 can contact or approach the sheet P. As a result, while reducing or preventing disturbances such as deformation of the sheet P and entry of ambient light, precise sheet discrimination can be performed.

Further, in FIGS. 2A and 2B, the sheet information detecting sensor 110 is disposed on the upper side of the sheet discriminator 100 and the sheet loading table 120 is disposed on the lower side with the sheet discriminator 100 arranged therebetween. Specifically, the sheet loading table 120 is disposed below the sheet information detecting sensor 110. However, the positional relation of the sheet information detecting sensor 110 and the sheet loading table 120 is not limited thereto as long as a distance between the detection face of the sheet information detecting sensor 110 and the sheet P is secured and the detection face of the sheet information detecting sensor 110 can contact the sheet P.

However, the configuration in which the sheet information detecting sensor 110 is disposed above the sheet loading table 120 can avoid foreign materials brought into the sheet discriminator 100 via the sheet P and dust of the sheet P adhering and entering to the sheet information detecting sensor 110. Therefore, it is preferable that the sheet information detecting sensor 110 and the sheet loading table 120 have the positional relation as illustrated in FIGS. 2A and 2B Further, this configuration does not have any restriction in handling sheet discrimination. For example, no pressure is applied between the sheet information detecting sensor 110 and the sheet P, the sheet P is not deformed during a detecting operation, and a user does not have to apply any force when handling the sheet P. Therefore, data of the surface of the sheet P can be obtained easily.

It is to be noted that, at least, the sheet information detecting sensor 110 has a function to obtain information on the surface of the sheet P.

A light-emitting diode (LED) is generally employed as the light source 111 of the sheet information detecting sensor 110. By employing a surface emitting laser having VCSEL elements, surface information of the sheet P can be detected more precisely. Therefore, more precise detection results can be obtained.

Further, the sheet information detecting sensor 110 is preferably include at least a specular reflection light receiver (e.g., the receivers 113, 114, 115, and 118) to receive specular reflection light reflected on the sheet P and a diffused reflection light receiver (e.g., the receiver 113) to receive diffused reflection light reflected on the sheet P out of the light beams emitted from the light source 111 and irradiated to the sheet P. The sheet information detecting sensor 110 can be a known optical sensor. Since the sheet information detecting sensor 110 has multiple sensors disposed at different angles to detect scattered light beams of diffused reflection light, more precise detection results of information can be obtained than the information obtained from specular reflection light.

Figure 12A:
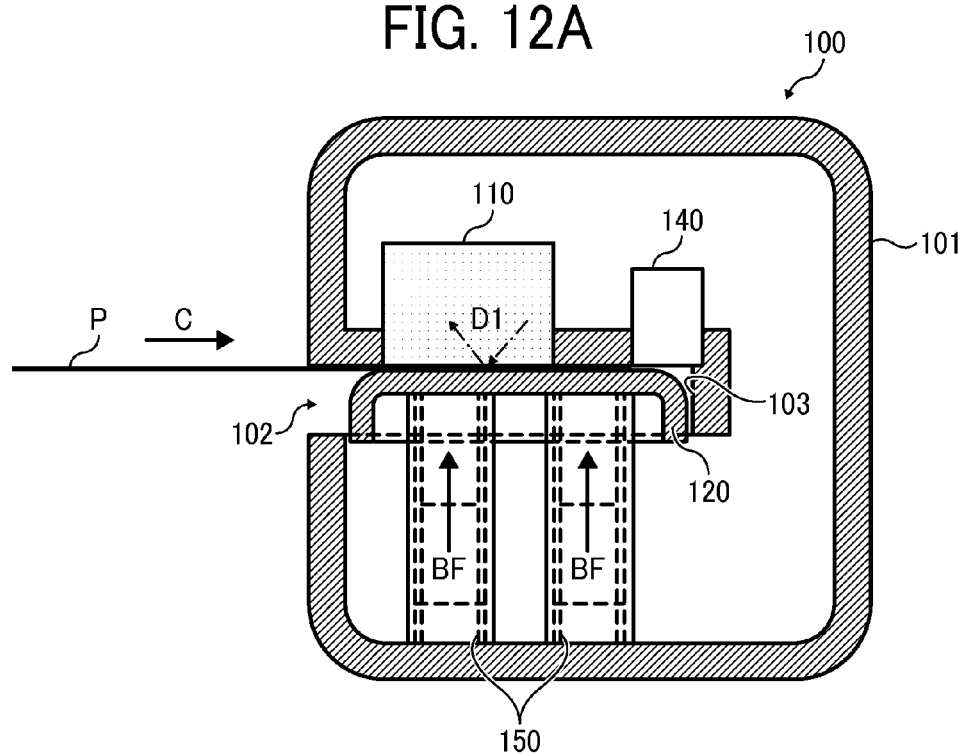
FIG. 12A is a cross sectional view illustrating a sheet discriminator according to another example of this disclosure, when the sheet is inserted into an opening.
Figure 12B:
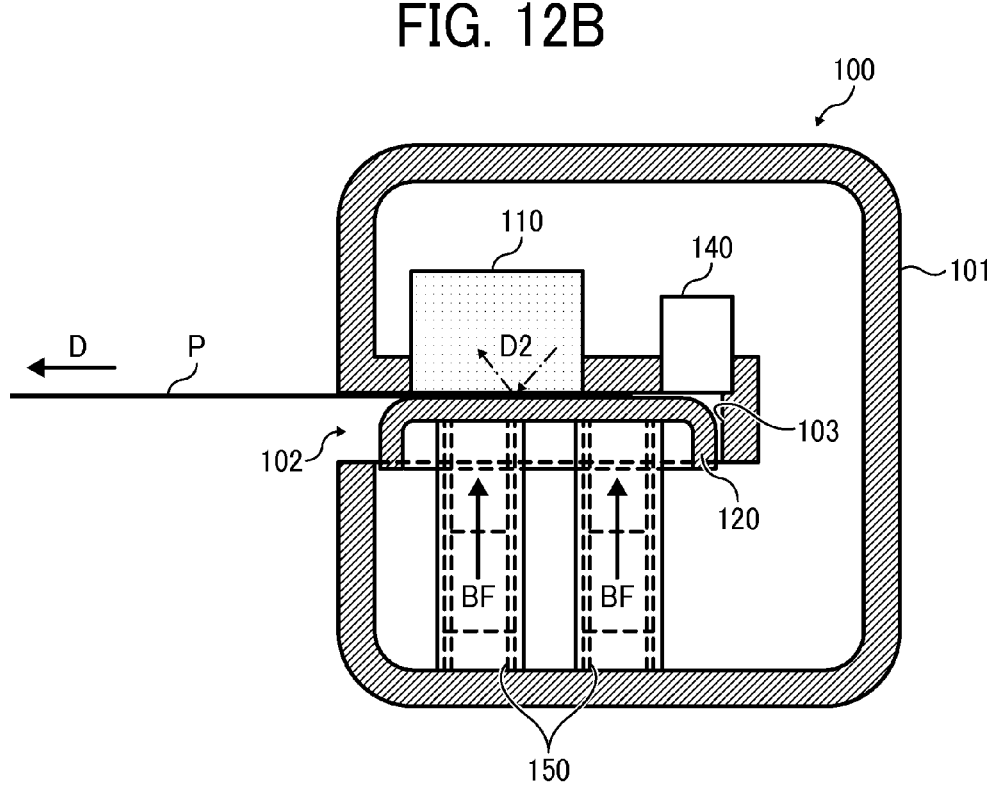
FIG. 12B is a cross sectional view illustrating the sheet discriminator of FIG. 12A when the sheet is pulled out from the opening of the sheet discriminator.

Now, a description is given of a sheet discriminator 100 according to another example of this disclosure, with reference to FIGS. 12A and 12B.

FIGS. 12A and 12B are cross sectional views of the sheet discriminator 100, viewed from a direction indicated by arrow A in FIG. 1. Specifically, FIG. 12A is a cross sectional view illustrating the sheet discriminator 100 when the sheet P is inserted thereto through the opening 102 of the sheet discriminator 100 and FIG. 2B is a cross sectional view illustrating the sheet discriminator 100 when the sheet P is pulled out from the opening 102 of the sheet discriminator 100.

In the sheet discriminator 100 according to this example, the sheet information detecting sensor 110 and the sheet detecting sensor 140 are aligned in this order in the sheet inserting direction indicated by arrow C illustrated in FIGS. 12A and 12B. Specifically, the positions of the sheet information detecting sensor 110 and the sheet detecting sensor 140 in the sheet inserting direction are switched from those illustrated in FIGS. 2A and 2B, and therefore the sheet detecting sensor 140 is disposed closer to the end face 103 than the sheet information detecting sensor 110 is.

It is to be noted that the configuration of the sheet discriminator 100 illustrated in FIGS. 12A and 12B is basically identical to the configuration of the sheet discriminator 100 illustrated in FIGS. 2A and 2B, except for the above-described positional relation of the sheet information detecting sensor 110 and the sheet detecting sensor 140. Therefore, detailed descriptions of the other components and functions are omitted here.

Next, a description is given of a control of sheet discrimination with reference to FIGS. 12A and 12B according to this example.

As illustrated in FIG. 12A, the sheet P is inserted toward the end face 103 of the opening 102 of the sheet discriminator 100 in the direction C. When the sheet P reaches the end face 103 of the opening 102, the sheet detecting sensor 140 detects the sheet P.

When the sheet detecting sensor 140 detects the sheet P, the sheet information detecting sensor 110 starts light emission and performs the first information detection D1 in FIG. 12A with respect to the sheet P.

After the sheet P has reached the end face 103 of the opening 102, the sheet P is removed. When pulling out the sheet P from the opening 102, the sheet P moves in the direction D in FIG. 12B. At this time, the sheet information detecting sensor 110 performs the second information detection D2 in FIG. 12B.

Accordingly, the sheet information detecting sensor 110 detects the sheet P at different points on the sheet P in the first information detection and the second information detection. As described above, the sheet discriminator 100 according to this example slides the sheet P in the opening 102 for multiple detections. Based on the information obtained by the sheet information detecting sensor 110, the controller 600 discriminates the sheet P.

After the sheet P is removed from the opening 102 and the sheet information detecting sensor 100 completed the second information detection D2, the controller 600 causes the sheet information detecting sensor 110 to stop light emission.

In the configuration according to this example, as illustrated in FIGS. 12A, and 12B, the sheet information detecting sensor 110 and the sheet detecting sensor 140 are aligned in this order in the sheet inserting direction indicated by arrow C illustrated in FIGS. 12A and 12B. Specifically, the sheet detecting sensor 140 is disposed closer to the end face 103 than the sheet information detecting sensor 110 is. Therefore, when the sheet P is detected by the sheet detecting sensor 140 detects the sheet P, the sheet P has reached a position facing the sheet information detecting sensor 110.

Therefore, when the sheet P is inserted into the opening 102, the controller 600 causes the sheet information detecting sensor 110 to start light emission in a state in which the sheet P has reached a position facing the sheet information detecting sensor 110.

Accordingly, the above-described configuration of the sheet discriminator 100 illustrated in FIGS. 12A and 12B can reduce a time period from the start of light emission of the sheet information detecting sensor 110 to the detection when compared with the configuration of the sheet discriminator 100 illustrated in FIGS. 2A and 2B in which the sheet information detecting sensor 110 starts light emission and the sheet P reaches at the position facing the sheet information detecting sensor 110. Since the time of light emission of the sheet information detecting sensor 110 can be reduced, the sheet discriminator 100 according to this example can extend the life of the sheet information detecting sensor 110 and reduce waste energy consumption thereof.

Figure 13:
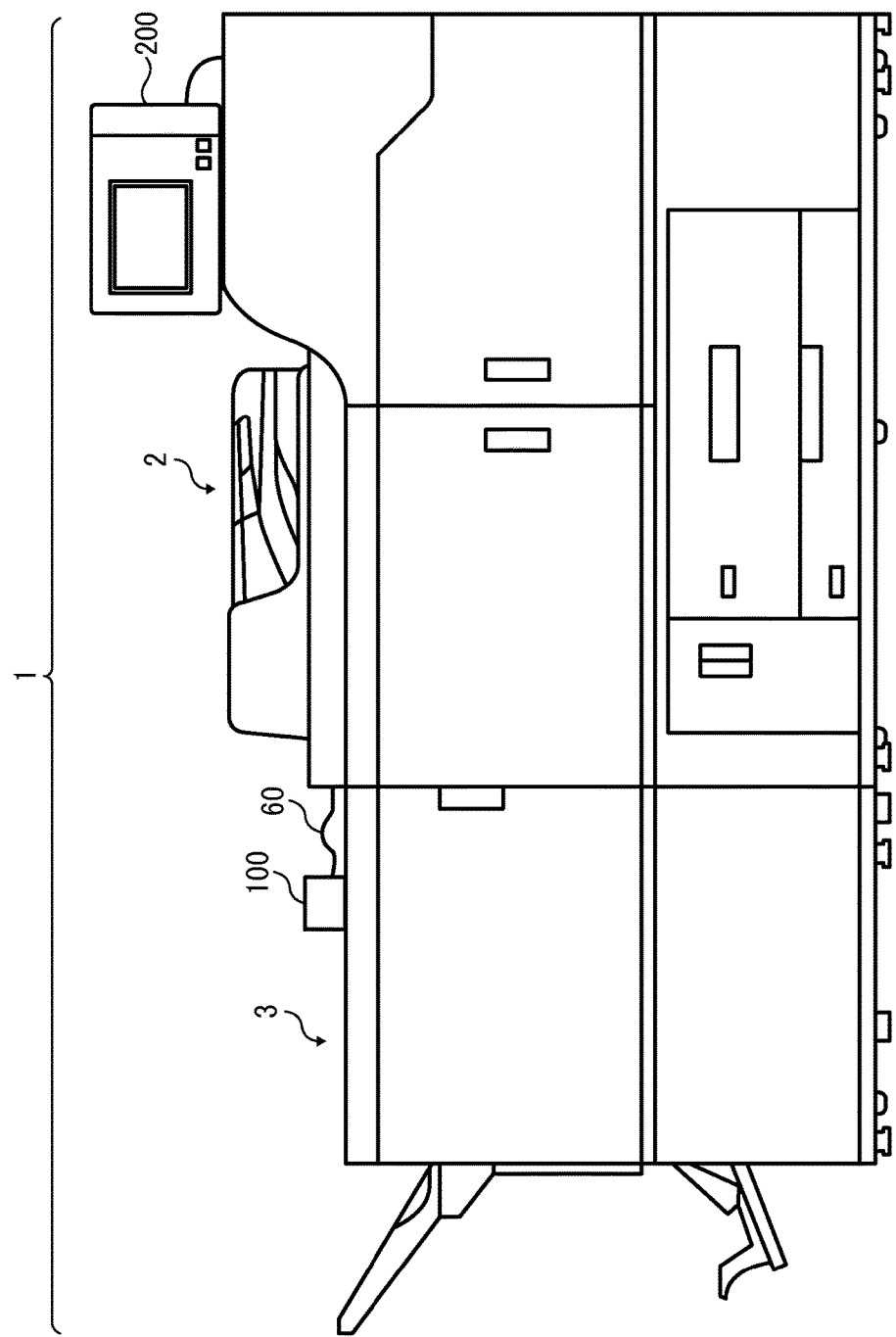
FIG. 13 is a diagram illustrating a configuration of an image forming system according to an example of this disclosure.

Next, a description is given of a configuration of an image forming system 1 according to another example of this disclosure, with reference to FIG. 13.

FIG. 13 is a diagram illustrating a configuration of an image forming system according to an example of this disclosure.

As illustrated in FIG. 13, the image forming system 1 includes an image forming apparatus 2 and a sheet finishing apparatus 3 that functions as a sheet finisher.

Further, the sheet discriminator 100 is disposed in the image forming system 1 outside the image forming apparatus 2.

The image forming apparatus 2 and the sheet finishing apparatus 3 are connected to communicate with each other. In the image forming system 1, after the image forming apparatus 2 has formed an image on the sheet P, the sheet finishing apparatus 3 accepts the sheet P from the image forming apparatus 2 for various post-processing operations to the sheet P.

The post-processing operations include, for example, a corner binding process, a center folding process, and the like. The center folding process includes a center binding process. The sheet finishing apparatus 3 that executes the above-described various post-processing operations includes a sheet ejection mode, a corner binding mode, and a center binding mode.

Figure 14:
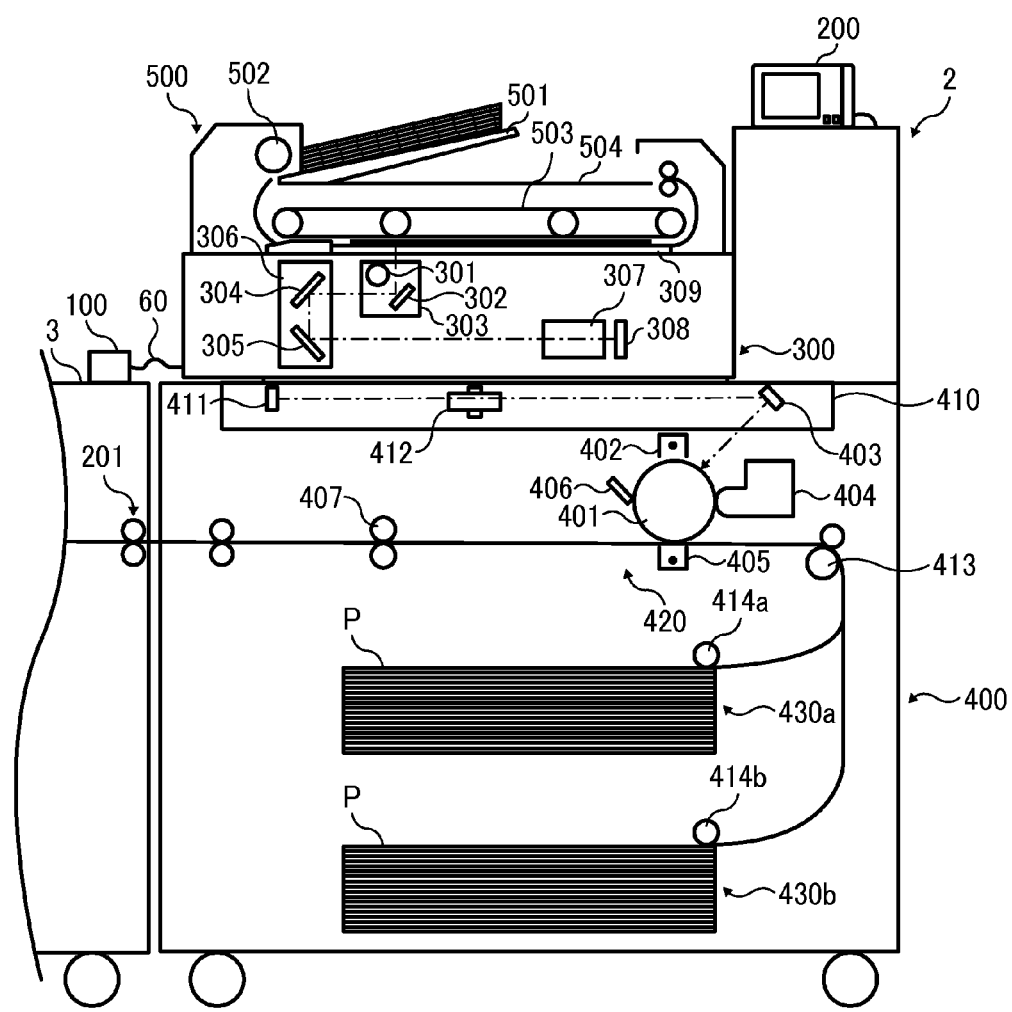
FIG. 14 is a diagram illustrating a configuration of an image forming apparatus included in the image forming system of FIG. 13.

FIG. 14 is a diagram illustrating a configuration of the image forming apparatus 2 included in the image forming system 1 of FIG. 13.

The image forming apparatus 2 may be a copier, a printer, a scanner, a facsimile machine, a plotter, and a multifunction peripheral or a multifunction printer (MFP) having at least one of copying, printing, scanning, facsimile, and plotter functions, or the like. According to the present example, the image forming apparatus 2 is an electrophotographic printer that forms toner images on a sheet or sheets by electrophotography.

More specifically, the image forming apparatus 2 functions as a printer. However, the image forming apparatus 2 can expand its function as a copier by adding a scanner as an option disposed on top of an apparatus body of the image forming apparatus 2. The image forming apparatus 2 can further obtain functions as a facsimile machine by adding an optional facsimile substrate in the apparatus body of the image forming apparatus 2.

Further, this disclosure is also applicable to image forming apparatuses adapted to form images through other schemes, such as known ink jet schemes, known toner projection schemes, or the like as well as to image forming apparatuses adapted to form images through electro-photographic schemes.

The image forming apparatus 2 includes an apparatus body 400, an image reading device 300, and an automatic document feeder (ADF) 500.

The apparatus body 400 encases an image forming part 420 and sheet trays 430a and 430b therein. The sheet trays 430a and 430b are vertically disposed below the image forming part 420. The sheet trays 430a and 430b have sheet feed rollers 414a and 414b, respectively, and accommodate the sheet P that functions as a recording medium. After the sheet P being fed by a selected one of the sheet feed rollers 414a and 414b, the sheet P accommodated in each of the sheet trays 430 is conveyed upwardly along a corresponding conveying path before reaching the registration roller pair 413.

The image forming part 420 includes a photoconductor drum 401 that functions as an image bearer, a charger 402, an exposing device 410, a developing device 404, a transfer device 405, and a cleaning device 406.

The charger 402 uniformly charges a surface of the photoconductor drum 401.

The exposing device 410 is a latent image forming device to form an electrostatic latent image on the surface of the photoconductor drum 401 based on image data read by the image reading device 300.

The developing device 404 supplies toner to adhere to the electrostatic latent image formed on the surface of the photoconductor drum 401 and develops the electrostatic latent image into a visible toner image.

The transfer device 405 is an image transfer body to transfer the visible toner image on the photoconductor drum 401 onto the sheet P.

The cleaning device 406 is a cleaner to remove residual toner remaining on the surface of the photoconductor drum 401 after transfer of the toner image onto the sheet P.

The image forming apparatus 2 further includes a fixing device 407 that is disposed downstream from the image forming part 420 in a sheet conveying direction. The fixing device 407 functions as a fuser to fix the toner image to the sheet P.

The exposing device 410 include a laser unit 411 and a polygon mirror 412.

The laser unit 411 emits laser light based on the image data under control of a controller provided to the apparatus body 400.

The polygon mirror 412 scans the laser light emitted by the laser unit 411 in a direction of rotational axial of the photoconductor drum 401 (in a main scanning direction).

The image reading device 300 functions as an image reader to read image data of an original document.

The ADF 500 is disposed above the image reading device 300 and is connected to the image reading device 300. The ADF 500 includes a document table 501, a document feed roller 502, a transfer belt 503, and a document ejecting tray 504.

When original documents are set on the document table 501, upon receipt of a signal to start reading image data of the original documents, the document feed roller 502 of the ADF 500 feeds the original documents placed on the document table 501 one by one. Each original document fed by the document feed roller 502 is guided by the transfer belt 503 to a contact glass 309 and is halted on the contact glass 309 temporarily.

With the original document halted on the contact glass 309, the image reading device 300 reads the image data of the original document. Thereafter, the transfer belt 503 resumes to convey the original document to the document ejecting tray 504.

Next, a description is given of a series of image reading processes and a series of image forming processes.

Either when the ADF 500 feeds the original document to the contact glass 309 or when a user places the original document on the contact glass 309 manually and inputs a copy start instruction via the control panel 200, a light source 301 mounted on the first moving unit 303 emits light. Along with the light emission, the first moving unit 303 and the second moving unit 306 are moved along a guide rail.

As the light source 301 emits the light onto the original document placed on the contact glass 309, the reflection light reflects on the original document. The reflection light is guided to a mirror 302 mounted on the first moving unit 303 and mirrors 304 and 305 mounted on the second moving unit 306 to a lens 307 so as to be received by a CCD 308. As a result, the CCD 308 reads the image data of the original document and the read image data is converted from analog data to digital data by an analog/digital (A/D) conversion circuit provided to the image forming apparatus 2. The image data is then transmitted from a data output port of the image reading device 300 to the controller of the apparatus body 400.

By contrast, the apparatus body 400 starts driving the photoconductor drum 401. As the photoconductor drum 401 rotates at a given speed, the charger 402 uniformly charges the surface of the photoconductor 401. The exposing device 410 then exposes light to the surface of the photoconductor drum 401 to form the electrostatic latent image based on the image data read by the image reading device 300.

Then, the developing device 404 develops the electrostatic latent image formed on the surface of the photoconductor drum 401 into a visible toner image. The sheet P is fed from a selected one of the sheet trays 430a and 430b by a corresponding one of the sheet feed rollers 414a and 414b and temporarily stopped at the registration roller pair 413.

In synchronization with timing at which the leading end of the toner image formed on the surface of the photoconductor drum 401 reaches an image transfer part that is located facing the transfer device 405, the registration roller pair 413 conveys the sheet P to the image transfer part. When the sheet P passes the image transfer part, the toner image formed on the surface of the photoconductor drum 401 is transferred onto the sheet P due to an action of an electric field in a transfer nip region.

Thereafter, the sheet P having the toner image on the surface thereof is conveyed to the fixing device 407 so that the fixing device 407 fixes the toner image to the sheet P. Then, the sheet P is ejected to the sheet finishing apparatus 3.

It is to be noted that residual toner remaining on the surface of the photoconductor drum 401 without being transferred onto the sheet P at the image transfer part is removed from the photoconductor drum 401 by the cleaning device 406.

Figure 15:
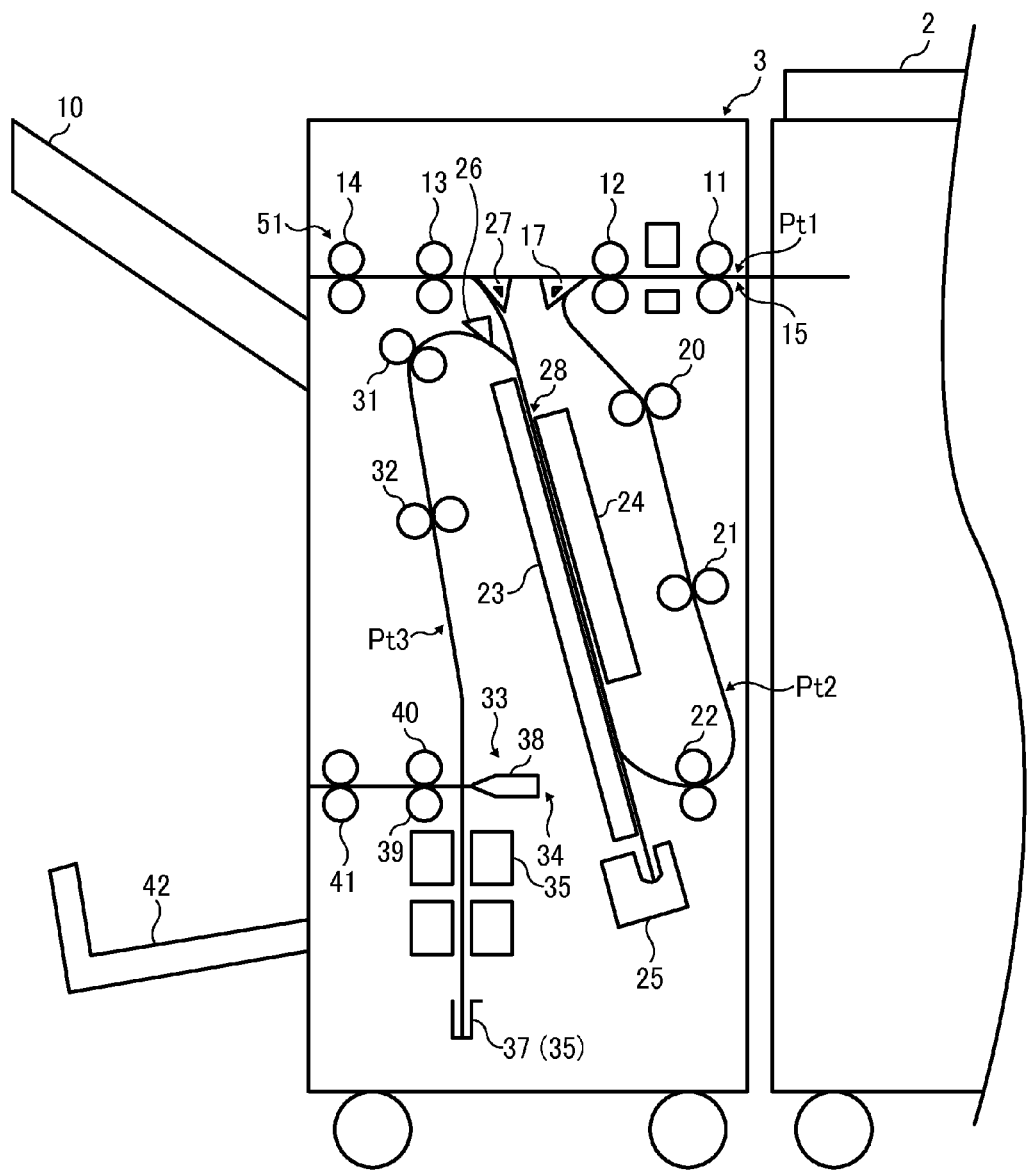
FIG. 15 is a diagram illustrating a configuration of a sheet finisher included in the image forming system of FIG. 13.

A description is given of the sheet finishing apparatus 3 with reference to FIG. 15.

FIG. 15 is a diagram illustrating a configuration of the sheet finishing apparatus 3 included in the image forming system 1 illustrated in FIG. 13.

The sheet finishing apparatus 3 includes a first conveying path Pt1, a second conveying path Pt2, and a third conveying path Pt3. The first conveying path Pt1 is a path through which the sheet P ejected from the image forming apparatus 2 travels to the first sheet ejecting tray 10. The second conveying path Pt2 branches from the first conveying path Pt1 to perform a saddle-stitching operation to a bundle of sheets. The third conveying path Pt3 is connected to the second conveying path Pt2 to perform a saddle-stitched center-folded sheet bundling operation to the bundle of sheets.

The first conveying path Pt1, the second conveying path Pt2, and the third conveying path Pt3 are defined by guide members, for example.

The first conveying path Pt1 includes an entrance roller 11, a sheet conveying roller 12, a sheet conveying roller 13, and a sheet ejecting roller 14, which are disposed in this order along the first conveying path Pt1 from an upstream side to a downstream side of the sheet conveying direction.

The entrance roller, the sheet conveying roller 12, the sheet conveying roller 13, and the sheet ejecting roller 14 are driven by a motor that functions as a driving source to convey a sheet of paper.

The first conveying path Pt1 further includes an entrance sensor 15 disposed upstream from the entrance roller 11 in the sheet conveying direction. The entrance sensor 15 detects that the sheet P is conveyed into the sheet finishing apparatus 3.

A bifurcating claw 17 is disposed downstream from the sheet conveying roller 12 in the sheet conveying direction. The bifurcating claw 17 switches the position by rotating to selectively guide the sheet P to one of a downstream side of the bifurcating claw 17 in the first conveying path Pt1 in the sheet conveying direction and the second conveying path Pt2. The bifurcating claw 17 is driven by a motor or a solenoid.

In a sheet ejecting mode, the sheet P conveyed from the image forming apparatus 2 to the first conveying path Pt1 is conveyed by the entrance roller 11, the sheet conveying roller 12, the sheet conveying roller 13, and the sheet ejecting roller 14 and is ejected to the first sheet ejecting tray 10.

By contrast, in a side stitching mode and a saddle stitching mode, the sheet P entered into the first conveying path Pt1 is conveyed by the entrance roller 11 and the sheet conveying roller 12, has a course of direction changed by the bifurcating claw 17, and is conveyed to the second conveying path Pt2.

The second conveying path Pt2 includes a sheet conveying roller 20, a sheet conveying roller 21, a sheet conveying roller 22, a sheet tray 23, a first sheet aligning part 24, and a side-stitching unit (a first stitching unit) 25.

The sheet conveying roller 20, the sheet conveying roller 22, and the conveying motor 22 are driven by a motor. The first sheet aligning part 24 is driven by the motor.

Bifurcating claws 26 and 27 are disposed at a downstream side of the sheet tray 23 in the sheet conveying direction. The bifurcating claws 26 and 27 rotate to switch respective positions, so that the sheet P is selectively guided to one of the downstream side of the bifurcating claw 17 in the first conveying path Pt in the first conveying path Pt1 and the third conveying path Pt3. The bifurcating claws 26 and 27 are driven by a motor or a solenoid, for example.

In the side stitching mode, multiple sheets P are sequentially loaded on the selected one of the sheet trays 23. By so doing, the bundle of sheets including the multiple sheets P loaded there on is formed. At this time, the trailing end of the bundle of sheets contacts a first movable reference fence that is disposed to the sheet tray 23 to align a position in the sheet conveying direction and a width position by the first sheet aligning part 24.

The sheet tray 23, the first sheet aligning part 24, and the first movable reference fence form a first bundling part 28 that functions as a bundling part to make multiple sheets into a stacked sheet bundle. The first bundling part 28 further includes a motor to drive the first sheet aligning part 24 and a motor to drive the first movable reference fence.

The side-stitched sheet bundle is conveyed by the first movable reference fence to the first conveying path Pt1. Then, the sheet bundle is further conveyed by the sheet conveying roller 13 and the sheet ejecting roller 14 to be ejected to the first sheet ejecting tray 10.

Here, the sheet ejecting roller 14 functions as a sheet ejecting member to eject the sheet bundle that is bundled by the side stitching unit 25. By contrast, in the center folding mode, the sheet P conveyed to the second conveying path Pt2 is conveyed to the third conveying path Pt3 by the sheet conveying rollers 20, 21, and 22, and the first movable reference fence.

The third conveying path Pt3 includes a sheet conveying roller 31, a sheet conveying roller 32, and a binding and folding part 33.

A motor drives the sheet conveying rollers 31 and 32 to convey the sheet P. The binding and folding part 33 includes a center folding part 34, a center folding part (a second stitching unit) 35, and a second bundling part 36.

The sheet P conveyed to the third conveying path Pt3 is conveyed by the sheet conveying rollers 31 and 32 one by one to the second bundling part 36. As a result, a sheet bundle of layered multiple sheets P is made. Specifically, the second bundling part 36 makes a stacked sheet bundle with multiple sheets conveyed by a sheet conveying part 51 that includes the entrance roller 11 and the sheet conveying rollers 12, 20, 21, 22, 31, and 32.

At this time, the leading end of the sheet bundle contacts a second movable reference fence 37 to be aligned in the sheet conveying direction and contacts a second sheet aligning part to be aligned in a sheet width direction.

The center folding part 35 stitches the sheet bundle at or in the vicinity of the center of the sheet bundle in the sheet conveying direction. The center-stitched sheet bundle is returned to a center folding position by the second movable reference fence 37. The second movable reference fence 37 is driven by a motor.

The center folding part 34 folds the sheet bundle at the center thereof in the sheet conveying direction. In the center folding part 34, a folding blade 38 is disposed to face the center of the sheet bundle in the sheet conveying direction. The folding blade 38 that is driven by a motor moves from right to left of FIG. 13 to fold the center of the sheet bundle in the sheet conveying direction to insert the sheet bundle between a lower pressure roller 39 and an upper pressure roller 40.

The folded sheet bundle is pressed by the lower pressure roller 39 and the upper pressure roller 40. The lower pressure roller 39 and the upper pressure roller 40 are driven by a motor.

The above-described center-folded sheet bundle is ejected by the lower pressure roller 39, the upper pressure roller 40, and a sheet ejecting roller 41 to a second sheet ejecting tray 42.

A description is given of another example of the sheet discriminator 100 according to this example.

Figure 17A:
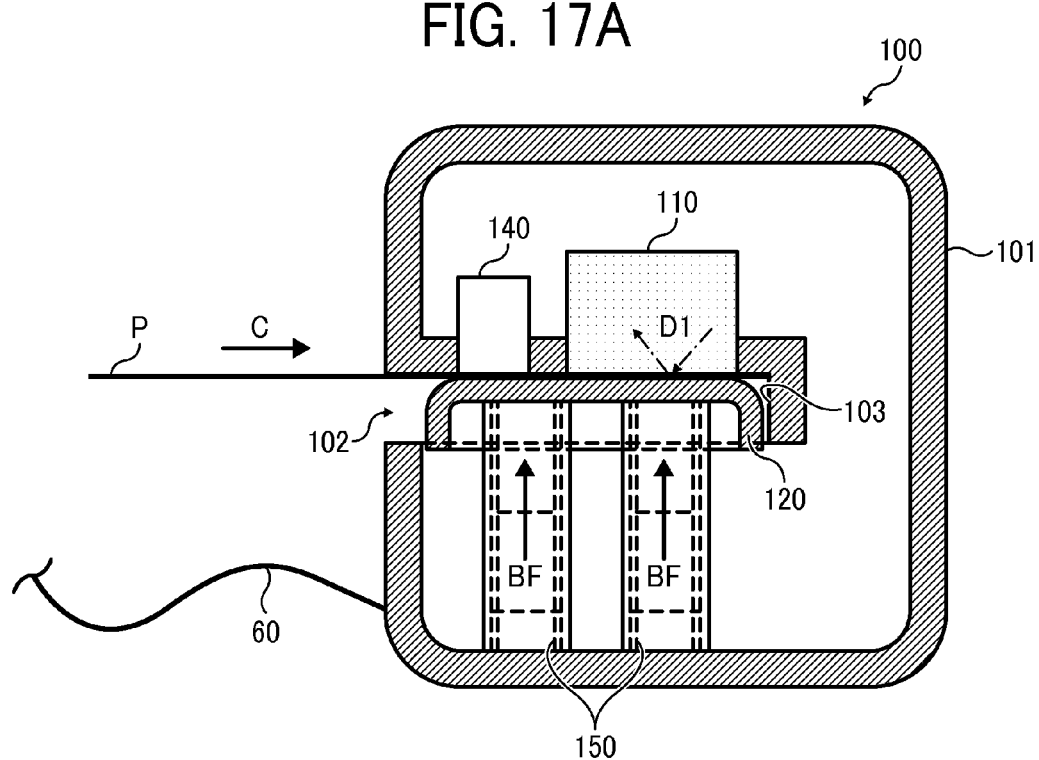
FIG. 17A is a cross sectional view illustrating the sheet discriminator when the sheet is inserted thereto through the opening.
Figure 17B:
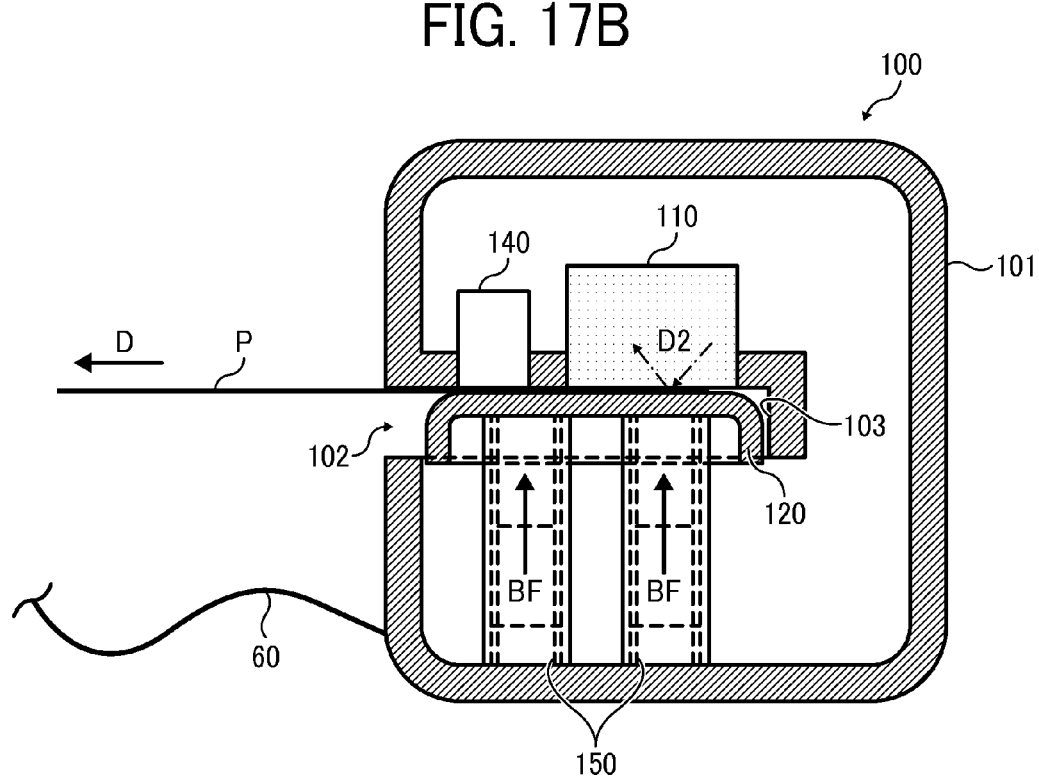
FIG. 17B is a cross sectional view illustrating the sheet discriminator when the sheet is pulled out from the opening of the sheet discriminator.

FIG. 17A is a cross sectional view illustrating the sheet discriminator 100 when the sheet P is inserted thereto through the opening 102. FIG. 17B is a cross sectional view illustrating the sheet discriminator 100 when the sheet P is pulled out from the opening 102 of the sheet discriminator 100.

It is to be noted that the basic configuration of the sheet discriminator 100 illustrated in FIGS. 17A and 18B is basically identical to the sheet discriminator 100 illustrated in FIGS. 2A and 2B, and therefore a detailed description of the configuration of the sheet discriminator 100 according to this example is omitted.

The sheet discriminator 100 according to this example is connected with the image forming apparatus 2 by a communication cable 60 that functions as a communicator. According to this configuration, the sheet discriminator 100 and the image forming apparatus 2 can communicate with each other.

The sheet P is inserted into the opening 102 of the sheet discriminator 100 that is connected to the image forming apparatus 2 via the communication cable 60 in the direction B until the sheet P contacts or approaches the end face 103 of the opening 102. By so doing, the sheet information related to sheet types determined by the sheet discriminator 100 according to this example is transmitted to the image forming apparatus 2 via the communication cable 60, so that appropriate image forming conditions can be set.

At this time, it is preferable that the operator grabs both left and right ends of the sheet P with respect to the direction B and inserts the sheet while checking that the sheet P has no deformation such as wrinkle or crease on the sheet P. It is to be noted that sheet insertion to the opening 102 is not limited to the above-described way but is applicable with any way of sheet insertion as long as the sheet P can be inserted into the opening 102 of the sheet discriminator 100 horizontally.

Figure 18:
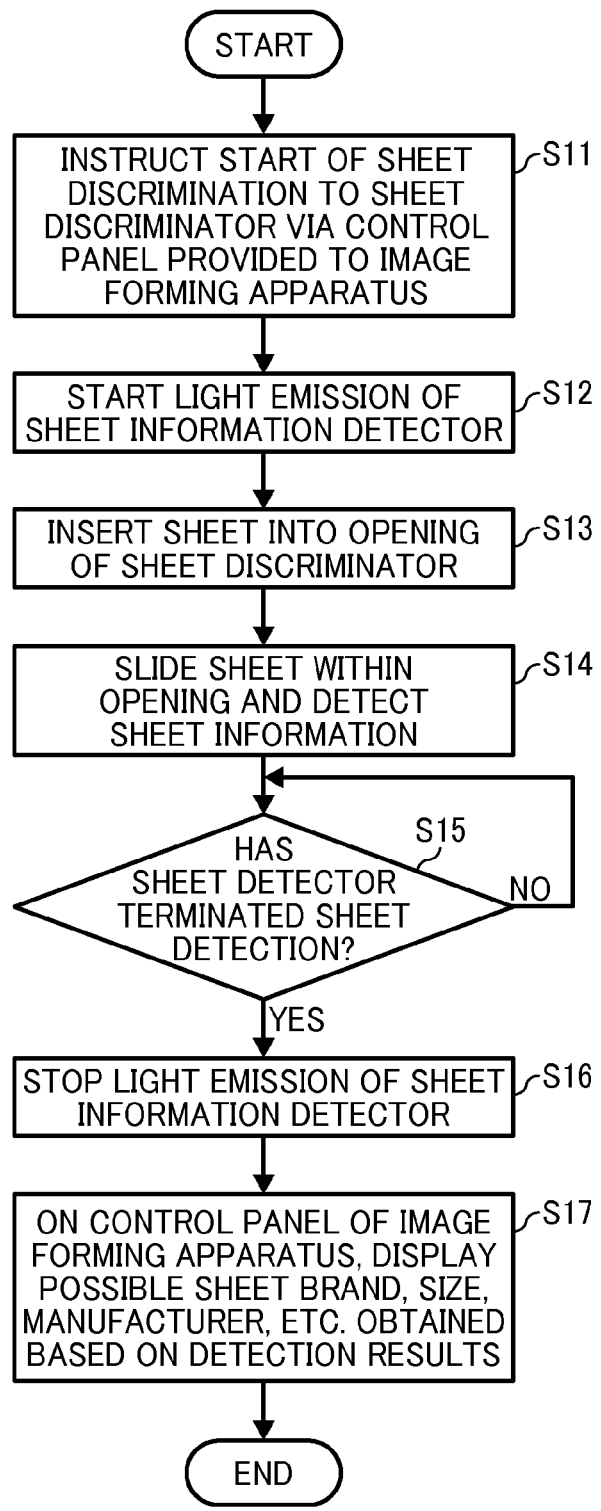
FIG. 18 is a flowchart illustrating an example of control of sheet discrimination performed by the sheet discriminator of FIG. 16.

A description is given of a control of sheet discrimination with reference to FIGS. 17A, 17B, and 18.

Figure 16:
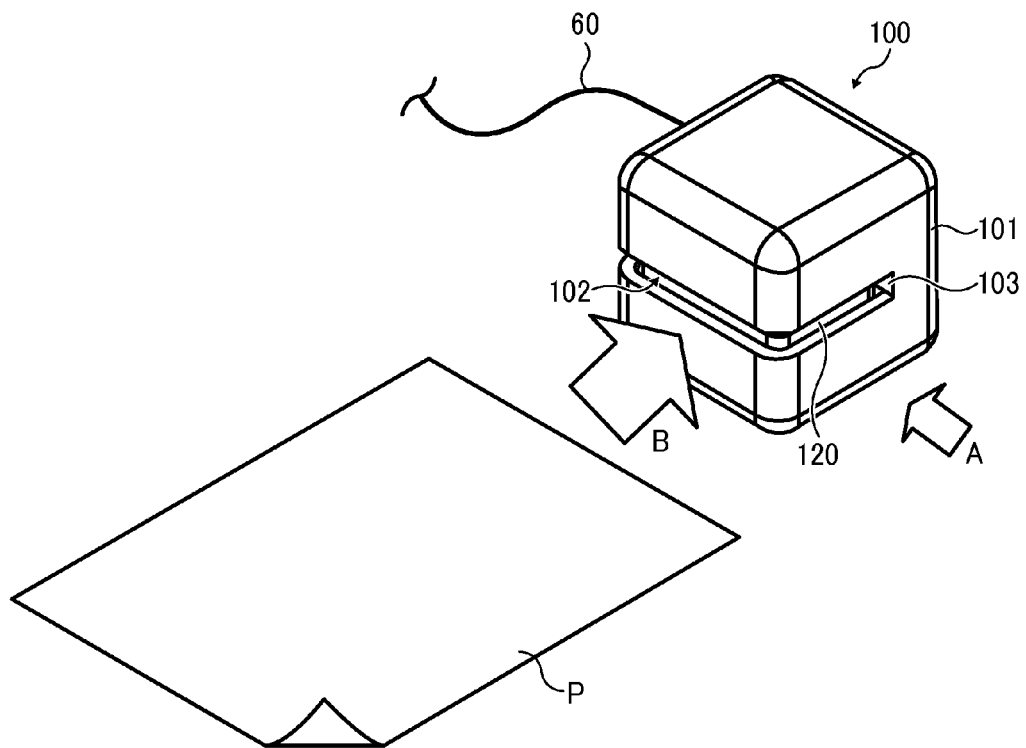
FIG. 16 is a diagram illustrating another configuration of a sheet discriminator included in the image forming system of FIG. 13.

FIGS. 17A and 17B are cross sectional views of the sheet discriminator 100, viewed from a direction indicated by arrow A in FIG. 16. Specifically, FIG. 17A is a cross sectional view illustrating the sheet discriminator 100 when the sheet P is inserted thereto through the opening 102 of the sheet discriminator 100 and FIG. 17B is a cross sectional view illustrating the sheet discriminator 100 when the sheet P is pulled out from the opening 102 of the sheet discriminator 100.

FIG. 18 is a flowchart illustrating an example of control of sheet discrimination performed by the sheet discriminator 100.

The sheet discriminator 100 receives instructions to start the sheet discrimination of the sheet P via the control panel 200 that is mounted on the image forming apparatus 2, as described in step S11 in the flowchart of FIG. 18. After the operation of step S11 in FIG. 18 is completed, the light emission processing unit 130 of the sheet discriminator 100 caused the sheet information detecting sensor 110 to start emitting light, as described in step S12 in the flowchart of FIG. 18. Then, as illustrated in FIG. 17A, the sheet P is inserted toward the end face 103 of the opening 102 of the sheet discriminator 100 in the direction C, as described in step S13 in the flowchart of FIG. 18.

The sheet information detecting sensor 110 performs the first information detection D1 in FIG. 17A with respect to the sheet P that is inserted toward the end face 103 of the opening 102. After the sheet P has reached the end face 103 of the opening 102, the sheet P is removed. When pulling out the sheet P from the opening 102, the sheet P moves in a direction indicated by arrow D in FIG. 17B. At this time, the sheet information detecting sensor 110 performs a second information detection D2 in FIG. 17B. Accordingly, the sheet information detecting sensor 110 detects the sheet P at different points on the sheet P in the first information detection and the second information detection.

As described above, the sheet discriminator 100 according to this example slides the sheet P in the opening 102 for multiple detections. Based on the information obtained by the sheet information detecting sensor 110, the controller 600 discriminates the sheet P, as described in step S14 in FIG. 18.

After the sheet P is removed from the opening 102 and is not detected by the sheet detecting sensor 140, which is YES in step S15 in FIG. 18, the light emission processing unit 130 causes the sheet information detecting sensor 110 to stop light emission, as described in step S16 in FIG. 18. When the sheet P is detected by the sheet detecting sensor 140, which is NO in step S15 in FIG. 18, the procedure is repeated until the sheet P is not detected by the sheet detecting sensor 140.

Further, based on detection results regarding the sheet P obtained by the sheet discriminator 100, possible sheet brands, sizes, manufacturers, etc. of the sheet P that is inserted into the sheet discriminator 100 through the opening 102 are displayed on a display of the control panel 200, as described in step S17. Then, the controller 600 completes the control of sheet discrimination using the sheet discriminator 100 illustrated in FIGS. 17A and 17B, and sets the image forming conditions according to a correct type of the sheet P out of the listed sheet brands, sizes, and so forth displayed on the control panel 200 to perform image formation.

Further, the sheet discriminator 100 according to this example causes the sheet information detecting sensor 110 to emit light when the sheet information detecting sensor 110 detects information of the sheet P. Accordingly, when compared with a case in which the sheet information detecting sensor 110 constantly emits light, the sheet discriminator 100 according to this example can extend the life of the sheet information detecting sensor 110 and reduce waste energy consumption thereof.

It is to be noted that the image forming apparatus 2 included in the image forming system 1 according to this example can be any one of a digital copier, a printer, an offset printer, and other image forming apparatuses.

It is also to be noted that the sheet discriminator 100 mounted on the image forming apparatus 2 can be any one of the sheet discriminators 100 according to the above-described examples of this disclosure.

The above-described embodiments are illustrative and do not limit this disclosure. Thus, numerous additional modifications and variations are possible in light of the above teachings. For example, elements at least one of features of different illustrative and exemplary embodiments herein may be combined with each other at least one of substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of this disclosure may be practiced otherwise than as specifically described herein.

What is claimed is:

1. A sheet information detecting device comprising:
   a housing having an opening thereon;
   an end face provided at a position opposite a leading end of a sheet in a sheet inserting direction when the sheet is inserted into the opening; and
   an information detector including a light emitter configured to emit light to a surface of the sheet inserted into the opening and a light receiver configured to receive reflected light emitted by the light emitter,
   the information detector configured to detect information of the sheet based on the reflected light while the leading end of the sheet is moving between the opening and the end face, wherein the information detector detects the information of the sheet while the sheet inserted into the opening is moving in a sheet removing direction in which the sheet separates from the end face, and wherein the information detector detects information of the sheet while the sheet is moving from the opening to the end face.

2. The sheet information detecting device according to claim 1, further comprising:
   a sheet detector configured to detect whether or not the sheet is located at a given detecting position; and
   a light emission controller configured to activate the light emitter when the sheet detector detects the sheet.

3. The sheet information detecting device according to claim 2, wherein the sheet detector is disposed closer to the end face than the information detector.

4. The sheet information detecting device according to claim 2, wherein, when the information detector completes detection of the sheet, the light emission controller causes the light emitter to stop light emission.

5. The sheet information detecting device according to claim 1, wherein the sheet detector is disposed closer to the opening than the information detector.

6. The sheet information detecting device according to claim 1, wherein the information detector performs multiple detections while the sheet is moving in different directions.

7. The sheet information detecting device according to claim 6, wherein, when the sheet inserted into the opening is moving in the sheet removing direction, the information detector performs multiple detections.

8. The sheet information detecting device according to claim 1, further comprising a transmitted light receiver configured to receive transmitted light emitted by the light emitter through the sheet.

9. The sheet information detecting device according to claim 1, wherein the light emitter emits laser light.

10. The sheet information detecting device according to claim 1, wherein the light receiver of the information detector has multiple light receivers, and wherein the multiple light receivers include:
    at least a specular reflected light receiver configured to directly receive specular reflected light emitted from the light emitter and reflected on the sheet; and
    at least a filtered diffused reflected light receiver configured to receive diffused and reflected light emitted from the light emitter and reflected on the sheet.

11. The sheet information detecting device according to claim 1, wherein the light receiver of the information detector has multiple light receivers, and wherein the multiple light receivers include at least a light receiver configured to receive a given component of polarized light out of light reflected on the sheet.

12. An image forming system comprising:
    an image former configured to form an image on the sheet; and
    the sheet information detecting device according to claim 1.

13. The image forming system according to claim 12, wherein an image forming condition of the image former is changed based on a detection result of the information detector.

* * * * *